United States Patent
Doerflinger et al.

(10) Patent No.: US 7,772,261 B2
(45) Date of Patent: Aug. 10, 2010

(54) PYRAZOLO[4,3-D]THIAZOLE DERIVATIVES, AND PREPARATION AND THERAPEUTIC APPLICATION THEREOF

(75) Inventors: Gilles Doerflinger, Paris (FR); Jean-Christophe Carry, Paris (FR)

(73) Assignee: sanofi-aventis, Paris (FR)

( * ) Notice: Subject to any disclaimer, the term of this patent is extended or adjusted under 35 U.S.C. 154(b) by 0 days.

(21) Appl. No.: 12/356,740

(22) Filed: Jan. 21, 2009

(65) Prior Publication Data

US 2009/0176779 A1 Jul. 9, 2009

Related U.S. Application Data

(63) Continuation of application No. PCT/FR2007/001326, filed on Jul. 31, 2007.

(30) Foreign Application Priority Data

Aug. 3, 2006 (FR) .................................. 06 07128

(51) Int. Cl.
*C07D 513/04* (2006.01)
*A61K 31/4162* (2006.01)
*A61K 31/429* (2006.01)

(52) U.S. Cl. ..................... 514/367; 548/153; 548/360.5

(58) Field of Classification Search ....................... None
See application file for complete search history.

(56) References Cited

U.S. PATENT DOCUMENTS

| 7,300,949 B2 * | 11/2007 | Barbosa et al. ............. 514/366 |
|---|---|---|
| 2005/0026984 A1 | 2/2005 | Bigot et al. |
| 2005/0176786 A1 | 8/2005 | Bounaud et al. |
| 2005/0187209 A1 | 8/2005 | Fancelli et al. |

FOREIGN PATENT DOCUMENTS

| EP | 1 510 516 A1 | 3/2005 |
|---|---|---|
| FR | 2 411 188 | 7/1979 |
| WO | WO 95/04729 | 2/1995 |
| WO | WO 2004/013146 A1 | 2/2004 |
| WO | WO 2005/068473 A1 | 7/2005 |
| WO | WO 2005/074922 A1 | 8/2005 |
| WO | WO 2005/095420 A1 | 10/2005 |
| WO | WO 2005/113494 A2 | 12/2005 |
| WO | WO 2007/059341 A2 | 5/2007 |

OTHER PUBLICATIONS

Byrn et al. Solid-State Chemistry of Drugs, 2d, Chapter 11 Hydrates and Solvates/hydrates, 233-247 (1999).*
Morissette et al. Adv. Drug Delivery Rev. 56, 275-300 (2004).*
Rouhi, Chem. & Eng. News, 81(8), 32-35 (Feb. 24, 2003).*
Albericio et al, An Improved Synthesis of N-[(9-hydroxymethyl)-2-fluorenyl]succinamic Acid (HMFS), A Versatile Handle for the Solid-Phase Synthesis of Biomolecules, Synthetic Comm., 2001 (31) 2 pp. 225-232.

Asahara et al, Tie2 Receptor Ligands, Angiopoietin-1 and Angiopoietin-2, Modulate VEGF-Induced Postnatal Neovascularization, Circ. Res., 1998, pp. 233-240.
Bischoff et al, A homologue of *Drosophila aurora* kinase is oncogenic and amplified in human colorectal cancers, EMBO Journal, vol. 17, No. 11, 1998,—3052-3065.
Cai et al, Preparation of N-Aryl Compounds by Amino Acid-Promoted Ullmann-Type Coupling Reactions, Synthesis 2005 (3) pp. 0496-0499.
Daidone et al, Synthesis, Crystallographic Studies and Biological Evaluation of some 2-Substituted 3-Indazolyl-4(3H)-Quinazolinones and 3-Indazolyl-4(3H)-Benzotriazinones, Heterocycles 1996 (43) 11 pp. 2385-2396.
Davis et al, Isolation of Angiopoietin-1, a Ligand for the TIE2 Receptor, by Secretion-Trap Expression Cloning, Cell, 1996 (87) pp. 1161-1169.
Dondoni et al, Synthesis of (Trimethylsilyl)thiazoles and Reactions with Carbonyl Compounds. Selectivity Aspects and Synthetic Utility, J. Org. Chem., 1988 (53) pp. 1748-1761.
Dumont et al, Dominant-negative and targeted null mutations in the endothelial receptor tyrosine kinase, tek, reveal a critical role in vasculogenesis of the embryo, Genes Dev., 1994 (8) pp. 1897-1909.
Kwong, et al., Copper-Catalyzed Coupling of Alkylamines and Aryl Iodides: An Efficient System Even in an Air Atmosphere, Organic Lett. 2002, 4 (4) pp. 581-584.
Lin et al, Antiangiogenic gene therapy targeting the endothelium-specific receptor tyrosine kinase Tie2, PNAS, 1998 (95) pp. 8829-8834.
Lin et al, Inhibition of Tumor Anglogenesis Using a Soluble Receptor Establishes a Role for Tie2 in Pathologic Vascular Growth, J. Clin. Invest., 1997 (100) 8 pp. 2072-2078.

(Continued)

*Primary Examiner*—Kamal A Saeed
*Assistant Examiner*—Michael Barker
(74) *Attorney, Agent, or Firm*—Kelly L. Bender

(57) ABSTRACT

The disclosure relates to a compound of formula (I):

(I)

in which:
$R_1$, $R_2$, $R_3$ and $R_4$ are as described in the specification, to compositions containing them and to their therapeutic use, especially as anticancer agents. The disclosure also relates to the process for preparing these compounds and to certain intermediate products.

22 Claims, No Drawings

OTHER PUBLICATIONS

Ma et al, Mild Method for Ullmann Coupling Reaction of Amines and Aryl Halides, Organic Letters, 2003 (5) 14 pp. 2453-2455.

Maisonpierre et al, Angiopoietin-2, a Natural Antagonist for Tie2 That Disrupts in vivo Angiogenesis, Science, 1997 (277) pp. 55-60.

Procter et al, Beta-Lactams from Tetrahydro-1,2-oxazine-3,6-diones, and a Labelling Study of the Product Stereochemistry, Tetrahedron 1995 (51) 47 pp. 12837-12842.

Schroeder et al, Liquid Crystals. 6. Mesomorphic Phenols and Primary Amines. p-Phenylene Dibenzoates with Terminal Hydroxy and Amino Groups, J. Org. Chem., 1976 (41) 15 pp. 2566-2571.

Suri et al, Requisite Role of Angiopoietin-1, a Ligand for the TIE2 Receptor, during Embryonic Angiogenesis, Cell, 1996 (87) pp. 1171-1180.

Urgaonkar et al, Application of a New Bicyclic Triaminophosphine Ligand in Pd-Catalyzed Buchwald-Hartwig Amination Reactions of Aryl Chlorides, Bromides, and Iodides, J. Org. Chem. 2003 (68) pp. 8416-8423.

Wolfe et al, Scope and Limitations of the Pd/BINAP-Catalyzed Amination of Aryl Bromides, J. Org. Chem., 2000 (65) pp. 1144-1157.

Wolfe et al, Simple, Efficient Catalyst System for the Palladium-Catalyzed Amination of Aryl Chlorides, Bromides, and Triflates, J. Org. Chem., 2000 (65) pp. 1158-1174.

Zim et al, An Air and Thermally Stable One-Component Catalyst for the Amination of Aryl Chlorides, Organic Letters, 2003 (5) 14 pp. 2413-2415.

* cited by examiner

PYRAZOLO[4,3-D]THIAZOLE DERIVATIVES, AND PREPARATION AND THERAPEUTIC APPLICATION THEREOF

This application is a continuation of International application No. PCT/FR2007/001326, filed Jul. 31, 2007, which is incorporated herein by reference in its entirety; which claims the benefit of priority of French Patent Application No. 0 607 128, filed Aug. 3, 2006.

FIELD OF THE INVENTION

The present invention relates to pyrazolo[4,3-d]thiazole derivatives, to compositions containing them and to their therapeutic use, especially as anticancer agents. The invention also relates to the process for preparing these compounds and to certain intermediate products.

BACKGROUND OF THE INVENTION

Most of the commercial compounds used to date in chemotherapy pose major problems of side effects and tolerance for the patients. The search for novel anticancer agents has turned in recent years towards therapies targeting enzymes or other biomolecules that are predominantly expressed and/or activated in cancer cells. A major class of enzymes that has been the subject of numerous studies is the family of protein kinases.

Patent application EP 1 510 516 describes JNK kinase-inhibiting compounds that may be used in neurodegenerative diseases (Alzheimer's disease, Parkinson's disease). Patent application WO 2004/013146 describes kinase-inhibiting compounds that may be used in cancer treatment. Patent application US 2005/0176786 describes tyrosine kinase-inhibiting compounds that may be used for treating cancer. Patent application US 2005/0187209 describes kinase-inhibiting compounds, especially Aurora 2, which may be used for treating cancer. Patent application WO 2005/095420 describes compounds that inhibit certain kinases, which may be used for treating psoriasis or brain cancer.

Patent applications WO 2005/074 922 and US 2005/0026984 describe compounds of thieno[2,3-d]pyrazole type. Patent application WO 2005/068473 describes, for X=S, compounds of the thiazolo[2,4-d]pyrazole type.

Patent application WO 2007/059341 describes compounds having the formula:

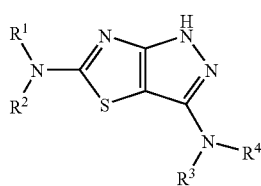

None of these documents describes or suggests the compounds of the thiazolo[4,3-d]pyrazole type of the present invention.

SUMMARY OF THE INVENTION

The invention relates to a compound of formula (I):

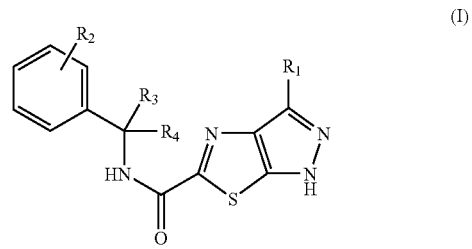

as defined herein. This compound may also exist in hydrate, solvate and/or addition-salt form.

The invention also relates to a medicament comprising the above compound and also to a pharmaceutical composition comprising the said compound and at least one pharmaceutically acceptable excipient.

The invention also relates to the use of the above compound for the preparation of a medicament for treating diseases in which metabolic enzymes chosen from kinases are involved. The medicament is intended for treating or preventing cancer.

The invention also relates to the process for obtaining the compound and also to certain intermediates.

DETAILED DESCRIPTION OF THE INVENTION

Definitions Used

In the context of the present invention, and unless otherwise mentioned in the text, the following definitions are used:
halogen atom: a fluorine, chlorine, bromine or iodine atom;
alkyl group: a linear or branched, saturated aliphatic hydrocarbon-based group, preferably containing from 1 to 20 carbon atoms, advantageously from 1 to 6 and preferably from 1 to 4 carbon atoms. Mention may be made especially of the following groups: methyl, ethyl, propyl, butyl, pentyl, hexyl, octyl, nonyl, decyl, dodecyl, hexadecyl, octadecyl, isopropyl, isobutyl, tert-butyl, 2-ethylhexyl;
alkenyl group: an alkyl group comprising one or more double bond(s). Mention may be made of the following groups: allyl, pentenyl, hexenyl, octenyl;
alkynyl group: an alkyl group comprising one or more triple bond(s) C≡C. Mention may be made especially of the following groups: hexynyl, heptynyl, octynyl;
haloalkyl group: an alkyl group as defined above, one or more hydrogen atoms of which have been replaced with at least one halogen atom. It preferably contains from 1 to 4 carbon atoms and from 1 to 6 halogen atoms. Mention may be made of the following groups: —CH$_2$F, CHF$_2$, —CF$_3$ and —CH$_2$CF$_3$;
alkoxy group: a group —O-alkyl in which the alkyl group is as defined above;
haloalkoxy group: an alkoxy group, one or more hydrogen atoms of which have been replaced with at least one halogen atom. It preferably contains from 1 to 4 carbon atoms and from 1 to 6 halogen atoms. Examples that may be mentioned include the groups —OCF$_3$, —OCH$_2$F and —OCHF$_2$;
cycloalkyl group: a cyclic alkyl group preferably containing from 3 to 8 carbon atoms engaged in the ring structure. Mention may be made especially of the following groups: cyclopropyl, cyclopentyl, cyclohexyl;

cycloalkenyl group: a cycloalkyl group as defined above comprising one or more double bond(s) C=C engaged in the ring;

aryl group: a cyclic aromatic group preferably containing from 6 to 14 carbon atoms. The aryl group is advantageously monocyclic or bicyclic. Mention may be made especially of the following groups: phenyl, naphthyl;

heteroaryl group: a 5- to 14-membered cyclic aromatic group comprising, as atoms forming the ring, one or more heteroatoms chosen from O, S and N. The heteroaryl group is advantageously monocyclic or bicyclic. It preferably contains between 2 and 13 carbon atoms and between 1 and 8 heteroatoms. Mention may be made of the following groups: pyridyl, pyrimidinyl, pyrazinyl, thiazolyl, imidazolyl, furyl and thienyl;

heterocycloalkyl group: a cycloalkyl group as defined above also comprising, as atoms forming the ring, one or more heteroatoms chosen from N, O and S. It preferably comprises from 1 to 4 heteroatoms. Mention may be made of the following groups: azetidinyl, pyrrolidinyl, piperidyl, morpholinyl and piperazinyl. The term "piperidyl" also means the N-alkylpiperidyls of formula

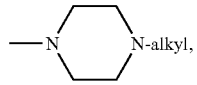

for example N-methylpiperidyl;

heterocycloalkenyl group: a heterocycloalkyl group as defined above comprising one or more double bond(s) C=C engaged in the ring;

$C_0$: represents a covalent bond or a hydrogen atom.

The following nomenclature is used in the present patent application to denote combinations of groups; for example: "-aryl-$(C_0$-$C_3)$alkyl-heterocycloalkyl group" denotes an aryl group linked either to an alkyl group, which is itself linked to a heterocycloalkyl group, or to a heterocycloalkyl group (in the case of $C_0$). For example, "-aryl-alkyl-cycloalkyl group" denotes an aryl group linked to an alkyl group which is itself linked to a cycloalkyl group.

According to a first aspect, a subject of the present invention is a compound of formula (I):

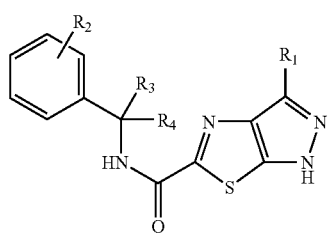

in which:
(i) $R_1$ represents a group —$NHR_5$, in which $R_5$ is selected from a hydrogen atom and a group —$COR_6$, in which $R_6$ is chosen from a hydrogen atom and an alkyl, alkenyl, alkynyl, cycloalkyl, cycloalkenyl, heterocycloalkyl, heterocycloalkenyl, aryl, heteroaryl, alkylaryl, alkylheteroaryl, -aryl-alkyl, -aryl-cycloalkyl, -aryl-alkyl-cycloalkyl, -aryl-heterocycloalkyl, -aryl-alkyl-heterocycloalkyl, -heteroaryl-alkyl, -heteroaryl-heterocycloalkyl or -heteroaryl-alkyl-heterocycloalkyl group, in which all the substituents $R_6$ are optionally substituted with one or more (for example 1 to 3) group(s), which may be identical to or different from each other, chosen from halogen atoms and alkoxy, oxo, —OH, —$CH_2OH$, —$NO_2$, —CN, —COOH, —COO-alkyl, haloalkyl (such as —$CH_2F$, —$CF_3$), haloalkoxy (such as —$OCF_3$, —$OCH_2F$, —$OCHF_2$), $CONR_7R_8$, $NR_7R_8$ and $S(O)_xMe$ groups, in which $R_7$ and $R_8$ represent, independently of each other, a hydrogen atom or an alkyl, cycloalkyl or haloalkyl group (such as a —$CF_3$ or —$CH_2$—$CF_3$ group) and in which x may take values from 0 to 2;

(ii) $R_2$ represents the possible substituent(s) of the phenyl ring that may be chosen, independently of each other when there are several of them, from a halogen atom, an alkyl, alkoxy, —OH, -haloalkyl (such as —$CF_3$ or —$CH_2$—$CF_3$), —$NO_2$, —CN or —COOH group or a group —COO-alkyl, haloalkoxy (such as —$OCF_3$, —$OCH_2F$ or —$OCHF_2$), -heteroaryl, -heterocycloalkyl, $CONR_7R_8$, $NR_7R_8$ or $S(O)_xMe$, in which the alkyl and alkoxy groups are optionally substituted with one or more (for example 1 to 3) groups, which may be identical to or different from each other, chosen from halogen atoms and alkoxy, —OH, haloalkyl (such as —$CF_3$), —$NO_2$, —CN, —COOH, —COO-alkyl, haloalkoxy (such as —$OCF_3$, —$OCH_2F$ or —$OCHF_2$), $CONR_7R_8$, $NR_7R_8$ and $S(O)_xMe$ groups, in which $R_7$, $R_8$ and x are as defined above;

(iii) $R_3$ and $R_4$ represent an alkyl group optionally substituted with one or more (for example 1 to 3) groups, which may be identical to or different from each other, chosen from halogen atoms and alkoxy, —OH, haloalkyl (such as —$CF_3$), —$NO_2$, —CN, —COOH, —COOalkyl, haloalkoxy (such as —$OCF_3$, —$OCH_2F$ or —$OCHF_2$), $CONR_7R_8$, $NR_7R_8$ and $S(O)_xMe$ groups, in which $R_3$ and $R_4$ form, together with the carbon to which they are attached, a 3- to 6-membered cycloalkyl group, such as cyclopropyl, cyclobutyl, cyclopentyl or cyclohexyl, optionally substituted with one or more groups, which may be identical to or different from each other, chosen from halogen atoms and -alkyl, -alkoxy, —OH, haloalkyl (such as a —$CF_3$ or —$CH_2$—$CF_3$ group), haloalkoxy (such as —$OCF_3$, —$OCH_2F$ or —$OCHF_2$), —$NO_2$, —CN, —COOH, —COO-alkyl, $CONR_7R_8$, $NR_7R_8$ and $S(O)_xMe$ groups, in which $R_7$, $R_8$ and x are as defined above.

More particularly:
(i) $R_1$ represents a group —$NHR_5$, in which $R_5$ is selected from a hydrogen atom and a group —$COR_6$, in which $R_6$ is chosen from a hydrogen atom and a group —$(C_1$-$C_6)$alkyl, —$(C_1$-$C_6)$alkenyl, —$(C_1$-$C_6)$alkynyl, —$(C_3$-$C_7)$cycloalkyl, —$(C_3$-$C_7)$cycloalkenyl, —$(C_3$-$C_7)$heterocycloalkyl, —$(C_3$-$C_7)$heterocycloalkenyl, —$(C_6$-$C_{14})$aryl, —$(C_4$-$C_{14})$heteroaryl, —$(C_1$-$C_6)$alkyl-aryl, —$(C_1$-$C_6)$alkyl-heteroaryl, -aryl-$(C_1$-$C_6)$alkyl, -aryl-$(C_0$-$C_3)$alkyl-cycloalkyl, -aryl-$(C_0$-$C_3)$alkyl-heterocycloalkyl, -heteroaryl-$(C_1$-$C_6)$alkyl or -heteroaryl-$(C_0$-$C_3)$alkyl-heterocycloalkyl in which all the substituents $R_6$ are optionally substituted with one or more (for example 1 to 3) group(s), which may be identical to or different from each other, chosen from halogen atoms and —$(C_1$-$C_6)$alkoxy, oxo, —OH, —$CH_2OH$, —$NO_2$, —CN, —COOH, —COO—$(C_1$-$C_4)$alkyl, haloalkyl (such as —$CH_2F$ or —$CF_3$), haloalkoxy (such as —$OCF_3$, —$OCH_2F$ or —$OCHF_2$), $CONR_7R_8$, $NR_7R_8$ and $S(O)_xMe$ groups, in which $R_7$ and $R_8$ represent, independently of each other, a hydrogen atom or a —$(C_1$-$C_4)$alkyl, cycloalkyl or haloalkyl group (such as a —CF$_3$ or —CH$_2$—CF$_3$ group) and in which x may take the values from 0 to 2;

and/or (ii) R$_2$ represents the possible substituents(s) of the phenyl ring that may be chosen, independently of each other when there are several of them, from a halogen atom, a —(C$_1$-C$_4$)alkyl, —(C$_1$-C$_6$)alkoxy, —OH, haloalkyl (such as —CF$_3$), —NO$_2$, —CN or —COOH group and a group —COO—(C$_1$-C$_4$)alkyl, haloalkoxy (such as —OCF$_3$, —OCH$_2$F or —OCHF$_2$), —(C$_4$-C$_{14}$)heteroaryl, —(C$_3$-C$_7$)heterocycloalkyl, —CONR$_7$R$_8$, —NR$_7$R$_8$ and —S(O)$_x$Me, in which the alkyl and alkoxy groups are optionally substituted with one or more (for example 1 to 3) group(s), which may be identical to or different from each other, chosen from halogen atoms and —(C$_1$-C$_4$)alkoxy, —OH, haloalkyl (such as —CF$_3$), —NO$_2$, —CN, —COOH, —COO—(C$_1$-C$_4$)alkyl, haloalkoxy (such as —OCF$_3$, —OCH$_2$F or —OCHF$_2$), —CONR$_7$R$_8$, —NR$_7$R$_8$ and —S(O)$_x$Me groups, in which R$_7$, R$_8$ and x are as defined above;

(i.e. R$_2$ represents a hydrogen or halogen atom, a —(C$_1$-C$_4$)alkyl, —(C$_1$-C$_6$)alkoxy, —OH, haloalkyl (such as —CF$_3$), —NO$_2$, —CN or —COOH group or a group —COO—(C$_1$-C$_4$)alkyl, haloalkoxy (such as —OCF$_3$, —OCH$_2$F or —OCHF$_2$), —(C$_4$-C$_{14}$)heteroaryl, —(C$_3$-C$_7$)heterocycloalkyl, —CONR$_7$R$_8$, —NR$_7$R$_8$ or —S(O)$_x$Me, in which the alkyl and alkoxy groups are optionally substituted with one or more (for example 1 to 3) group(s), which may be identical to or different from each other) chosen from halogen atoms and —(C$_1$-C$_4$)alkoxy, —OH, haloalkyl (such as —CF$_3$), —NO$_2$, —CN, —COOH, —COO—(C$_1$-C$_4$)alkyl, haloalkoxy (such as —OCF$_3$, —OCH$_2$F or —OCHF$_2$), —CONR$_7$R$_8$, —NR$_7$R$_8$ and —S(O)$_x$Me groups, in which R$_7$, R$_8$ and x are as defined above);

and/or (iii) R$_3$ and R$_4$ represent a —(C$_1$-C$_4$)alkyl group optionally substituted with one or more (for example 1 to 3) groups, which may be identical to or different from each other, chosen from halogen atoms and —(C$_1$-C$_4$)alkoxy, —OH, haloalkyl (such as —CF$_3$), —NO$_2$, —CN, —COOH, —COOalkyl, haloalkoxy (such as —OCF$_3$, —OCH$_2$F, or —OCHF$_2$), —CONR$_7$R$_8$, —NR$_7$R$_8$ and —S(O)$_x$Me groups, or R$_3$ and R$_4$ form, together with the carbon atom to which they are attached, a 3- to 6-membered cycloalkyl group such as cyclopropyl, cyclobutyl, cyclopentyl or cyclohexyl, optionally substituted with one or more group(s), which may be identical to or different from each other, chosen from halogen atoms and —(C$_1$-C$_4$)alkyl, —(C$_1$-C$_4$)alkoxy, —OH, haloalkyl (such as a —CF$_3$ or —CH$_2$—CF$_3$ group), haloalkoxy (such as —OCF$_3$, —OCH$_2$F or —OCHF$_2$), —NO$_2$, —CN, —COOH, —COO—(C$_1$-C$_4$)alkyl, —CONR$_7$R$_8$, —NR$_7$R$_8$ and —S(O)$_x$Me groups, in which R$_7$, R$_8$ and x are as defined above.

A subgroup of compounds in accordance with the invention that are particularly preferred is that in which R$_7$ and R$_8$ represent, independently of each other, a hydrogen atom or a —(C$_1$-C$_4$)alkyl group.

Another subgroup of compounds in accordance with the invention is that in which R$_3$ and R$_4$ each represent a methyl group.

Another subgroup of compounds in accordance with the invention is that in which R$_2$ represents a hydrogen atom (a non-substituted phenyl ring).

Mention may also be made of the subgroup of compounds in which R$_1$ represents a group —CO—R$_6$ in which R$_6$ is chosen from an aryl or heteroaryl group, optionally substituted with a halogen atom, —(C$_1$-C$_3$)alkoxy or —(C$_0$-C$_3$)alkyl-heterocycloalkyl (such as morpholinyl, piperazinyl, pyrrolidinyl or piperidyl). The aryl group is especially a phenyl and the heteroaryl group is a thienyl or a pyridine.

When R$_6$ represents an -aryl-(C$_0$-C$_3$)alkyl-heterocycloalkyl group or -heteroaryl-(C$_0$-C$_3$)alkyl-heterocycloalkyl, more particularly when aryl or heteroaryl denotes phenyl, thienyl or pyridine, the heterocycloalkyl comprises at least one nitrogen atom to which is attached the aryl, heteroaryl or alkyl group (i.e. the group is of the form

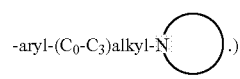

The heterocycloalkyl is more particularly morpholinyl, piperazinyl, pyrrolidinyl or piperidyl.

Mention may also be made of the subgroup of compounds in which R$_1$ represents a group —CO—R$_6$ in which R$_6$ represents a phenyl substituted with a group —(C$_1$-C$_3$)alkyl-NR$_9$R$_{10}$, more particularly —CH$_2$NR$_9$R$_{10}$, in which R$_9$ and R$_{10}$ are independently selected from the group consisting of H, —(C$_1$-C$_6$)alkyl, aryl, heteroaryl, —(C$_1$-C$_6$)alkyl-aryl, —(C$_1$-C$_6$)alkyl-heteroaryl, which are optionally substituted.

Mention may be made more particularly of the following compounds:

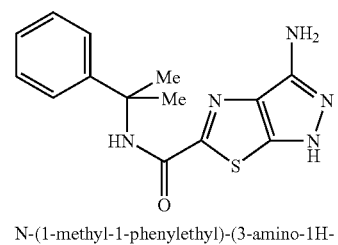

N-(1-methyl-1-phenylethyl)-(3-amino-1H-pyrazolo[4,3-d]thiazole)-5-carboxamide

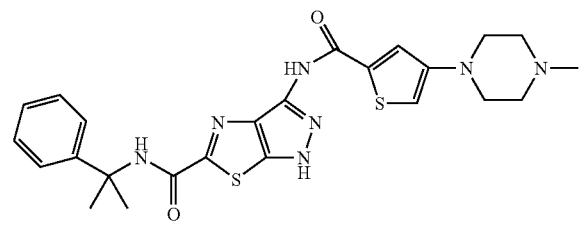

N-(1-methyl-1-phenylethyl)-3-{[4-(4-methylpiperazin-1-yl)thiophene-2-carbonyl]amino}-1H-pyrazolo[4,3-d]thiazole-5-carboxamide

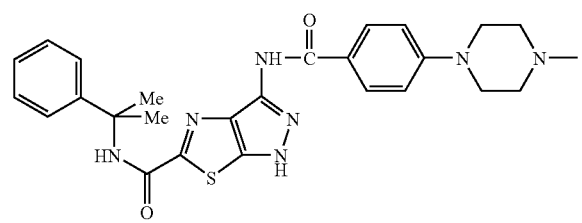

N-(1-methyl-1-phenylethyl)-3-[4-(4-methylpiperazin-1-yl)benzoylamino]1H-pyrazolo[4,3-d]thiazole-t-carboxamide -continued

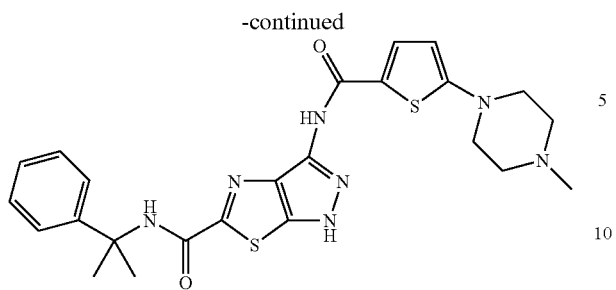

N-(1-methyl-1-phenylethyl)3-3{[5-(4-methylpiperazin-1-yl)thiophene-2-carbonyl]amino}-1H-pyrazolo[4,3-d]thiazole-5-carboxamide

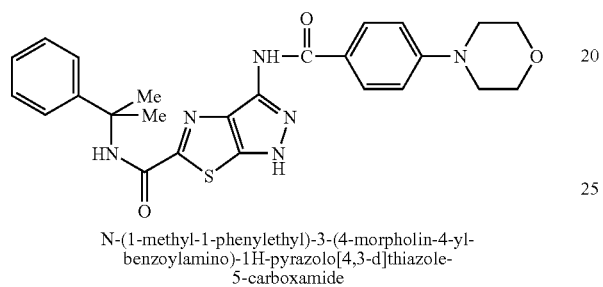

N-(1-methyl-1-phenylethyl)-3-(4-morpholin-4-yl-benzoylamino)-1H-pyrazolo[4,3-d]thiazole-5-carboxamide

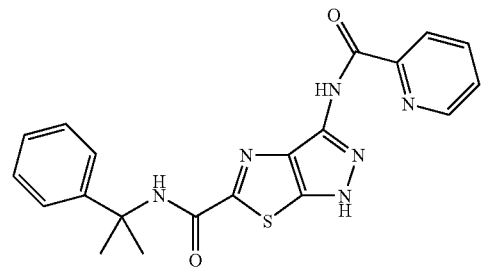

N-(1-methyl-1-phenylethyl)-3-[(pyridine-2-carbonyl)amino]-1H-pyrazolo[4,3-d]thiazole-5-carboxamide

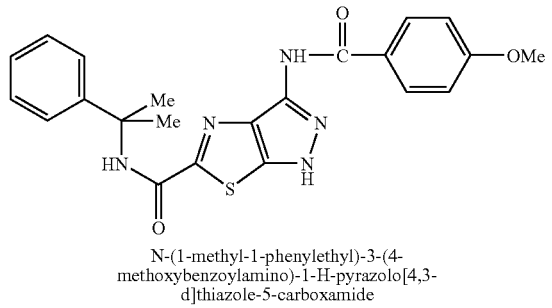

N-(1-methyl-1-phenylethyl)-3-(4-methoxybenzoylamino)-1-H-pyrazolo[4,3-d]thiazole-5-carboxamide

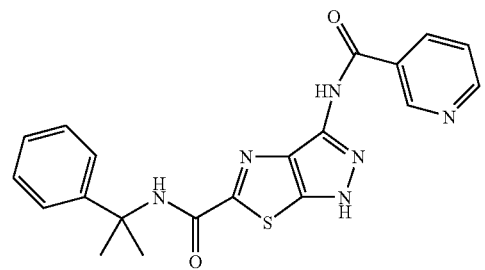

N-(1-methyl-1-phenylethyl)-3-[(pyridine-3-carbonyl)amino]-1H-pyrazolo[4,3-d]thiazole-5-carboxamide -continued

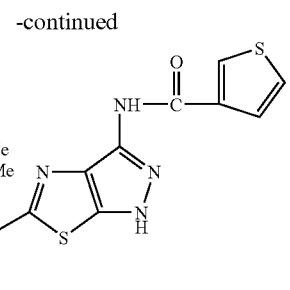

N-(1-methyl-1-phenylethyl)-3-[(thiophene-3-carbonyl)amino]-1H-pyrazolo[4,3-d]thiazole-5-carboxamide

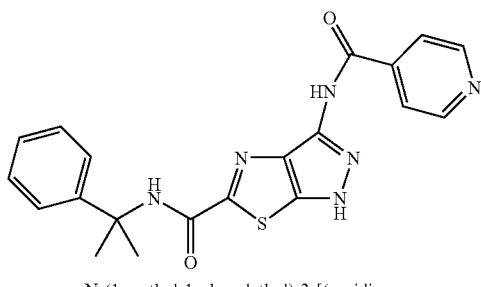

N-(1-methyl-1-phenylethyl)-3-[(pyridine-4-carbonyl)-amino]-1H-pyrazolo[4,3-d]thiazole-5-carboxamide

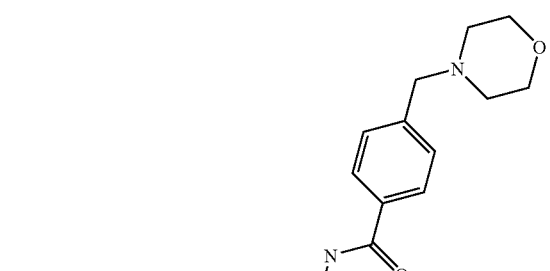

N-(1-methyl-1-phenylethyl)-3-(4-morpholin-4-ylmethylbenzoylamino)-1H-pyrazolo[4,3-d]thiazole-5-carboxamide

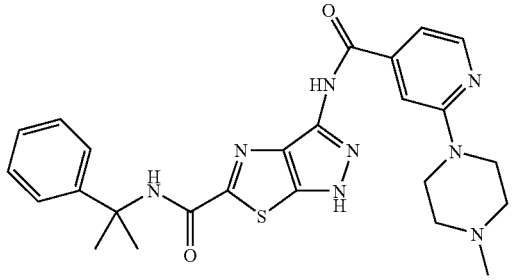

N-(1-methyl-1-phenylethyl)-3-{[2-(4-methylpiperazin-1-yl)pyridine-4-carbonyl]amino}-1H-pyrazolo[4,3-d]thiazole-5-carboxamide -continued

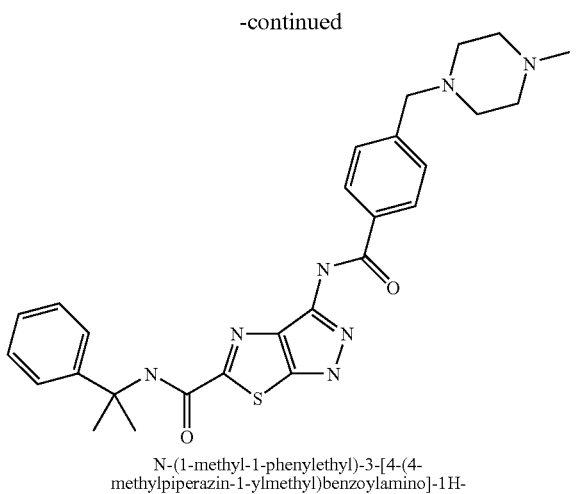

N-(1-methyl-1-phenylethyl)-3-[4-(4-methylpiperazin-1-ylmethyl)benzoylamino]-1H-pyrazolo[4,3-d]thiazole-5-carboxamide

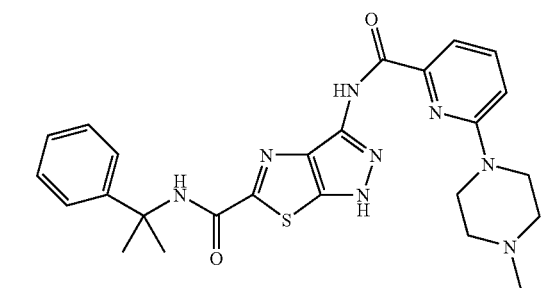

N-(1-methyl-1-phenylethyl)-3-{[6-(4-methylpiperazin-1-yl)pyridine-2-carbonyl]amino}-1H-pyrazolo[4,3-d]thiazole-5-carboxamide

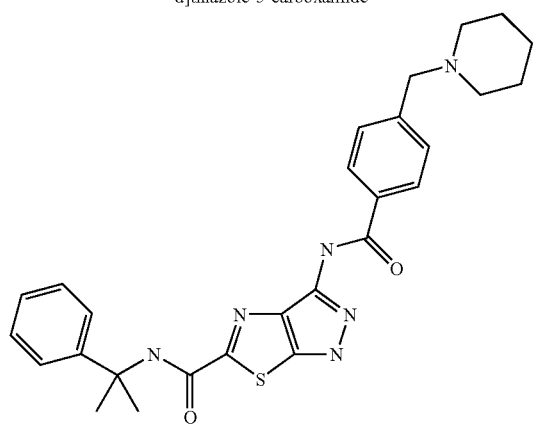

N-(1-methyl-1-phenylethyl)-3-(4-piperidin-1-ylmethylbenzoylamino)-1H-pyrazolo[4,3-d]thiazole-5-carboxamide

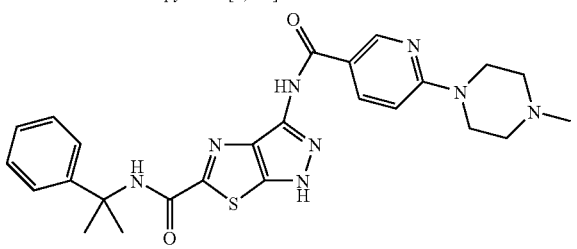

N-(1-methyl-1-phenylethyl)-3-{[6-(4-methylpiperazin-1-yl)pyridine-3-carbonyl]amino}-1H-pyrazolo[4,3-d]thiazole-5-carboxamide -continued

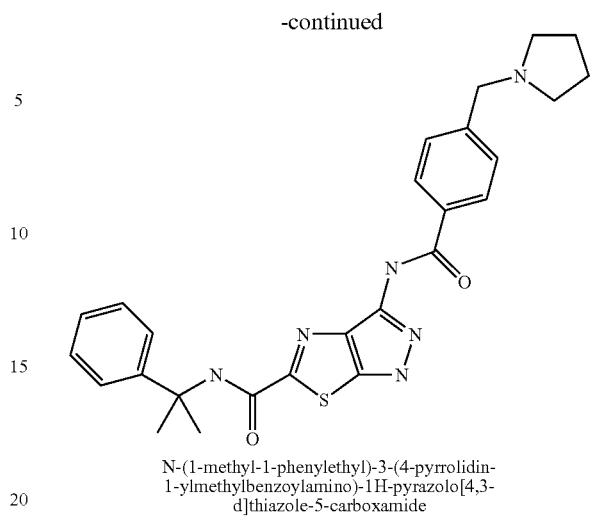

N-(1-methyl-1-phenylethyl)-3-(4-pyrrolidin-1-ylmethylbenzoylamino)-1H-pyrazolo[4,3-d]thiazole-5-carboxamide The compounds according to the invention may also exist in the form of hydrates or solvates, i.e. in the form of associations or combinations with one or more water molecules or with a solvent. Such hydrates and solvates also form part of the invention.

The compounds of the invention may also exist in the form of addition salts. The salts also form part of the invention. The compounds of the invention comprising a basic residue may be optionally converted into addition salts with a mineral or organic acid via the action of such an acid in an organic solvent such as an alcohol, a ketone, an ether or a chlorinated solvent. These salts are advantageously prepared with pharmaceutically acceptable acids, but salts of other acids that are useful, for example, for purifying or isolating the compounds of the invention, also form part of the invention. Pharmaceutically acceptable salts include the chlorides, nitrates, sulfates, hydrogen sulfates, pyrosulfates, bisulfates, sulfites, bisulfites, phosphates, monohydrogen phosphates, dihydrogen phosphates, metaphosphates, pyrophosphates, acetates, propionates, acrylates, 4-hydroxybutyrates, caprylates, caproates, decanoates, oxalates, malonates, succinates, glutarates, adipates, pimelates, maleates, fumarates, citrates, tartrates, lactates, phenylacetates, mandelates, sebacates, suberates, benzoates, phthalates, methanesulfonates, propanesulfonates, xylenesulfonates, salicylates, cinnamates, glutamates, aspartates, glucuronates and galacturonates.

The compounds of the invention comprising an acid residue may be optionally converted into metal salts or into addition salts with nitrogenous bases according to methods that are known per se. These salts may be obtained via the action of a metallic base (for example an alkali metal or an alkaline-earth metal), ammonia, an amine or an amine salt on a compound of formula (I), in a solvent. The salt formed is separated out via the usual methods. Pharmaceutically acceptable bases include hydroxides of alkali metal or alkaline-earth metal cations such as Li, Na, K, Mg or Ca, and basic amino compounds such as ammonia, arginine, lysine, histidine, piperidine, morpholine, piperazine or triethylamine.

Certain compounds according to the invention are themselves prodrugs of active parent compounds, in order to increase their oral bioavailability according to methods known to those skilled in the art.

According to a second aspect, the invention relates to a pharmaceutical composition comprising as active principle a compound according to the invention, in combination with a pharmaceutically acceptable excipient (according to the chosen mode of administration). The pharmaceutical composition may be in solid or liquid form or in the form of liposomes.

Among the solid compositions that may be mentioned are powders, gel capsules and tablets. Among the oral forms that may also be included are solid forms protected against the acidic medium of the stomach. The supports used for the solid forms especially consist of mineral supports, for instance phosphates or carbonates, or organic supports, for instance lactose, celluloses, starch or polymers. The liquid forms consist of solutions, suspensions or dispersions. They contain as dispersive support either water, or an organic solvent (ethanol, NMP or the like) or mixtures of surfactants and solvents or of complexing agents and solvents. The liquid forms will preferably be injectable and, as a result, will have a formulation that is acceptable for such a use.

Acceptable injection administration routes include the intravenous, intraperitoneal, intramuscular and subcutaneous routes, the intravenous route being preferred. The administered dose of the compounds of the invention will be adapted by the practitioner as a function of the route of administration to the patient and of the patient's condition.

The compounds of the present invention may be administered alone or as a mixture with at least one other anticancer agent. This agent may be chosen, for example, from:

an alkylating agent and especially cyclophosphamide, melphalan, ifosfamide, chlorambucil, busulfan, thiotepa, prednimustine, carmustine, lomustine, semustine, streptozotocin, decarbazine, temozolomide, procarbazine and hexamethylmelamine platinum derivatives such as, especially, cisplatin, carboplatin or oxaliplatin antibiotics such as, especially, bleomycin, mitomycin or dactinomycin antimicrotubule agents such as, especially, vinblastine, vincristine, vindesine, vinorelbine and taxoids (paclitaxel and docetaxel)

anthracyclines such as, especially, doxorubicin, daunorubicin, idarubicin, epirubicin, mitoxantrone and losoxantrone group I and II topoisomerase inhibitors such as etoposide, teniposide, amsacrine, irinotecan, topotecan and tomudex fluoropyrimidines such as 5-fluorouracil, UFT and floxuridine cytidine analogs such as 5-azacytidine, cytarabine, gemcitabine, 6-mercaptomurine and 6-thioguanine adenosine analogs such as pentostatin, cytarabine or fludarabine phosphate methotrexate and folinic acid various enzymes and compounds such as L-asparaginase, hydroxyurea, trans-retinoic acid, suramine, dexrazoxane, amifostine and herceptin, and also estrogen-based and androgenic hormones antivascular agents such as combretastatin derivatives or colchicine derivatives, and prodrugs thereof.

It is also possible to combine the compounds of the present invention with a radiation treatment. These treatments may be administered simultaneously, separately or sequentially. The treatment will be adapted by the practitioner as a function of the patient to be treated.

According to a third aspect, a subject of the invention is the use of a compound according to the invention for the manufacture of a medicament. Preferably, it may be useful for treating a pathological condition, in particular cancer.

According to a fourth aspect, a subject of the invention is the use of a compound according to the invention as a protein kinase inhibitor, preferably chosen from Aurora1, Aurora2 and Tie2. A particularly preferred kinase is Aurora2.

According to a fifth aspect, a subject of the invention is also the process for preparing the compounds according to the invention. The compounds of formula (I) may be prepared from the compounds of formula (Ia), according to Scheme 1:

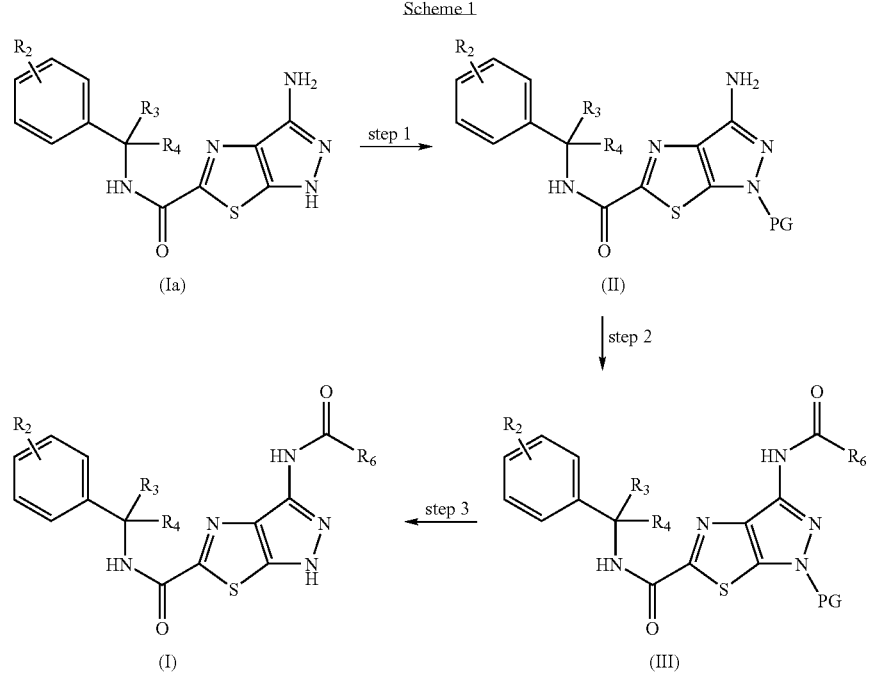

Step 1

Step 1 corresponds to a step of protecting the NH of the thiazole ring using the protecting group PG. The function of PG is to prevent unwanted side reactions during one or more reaction step(s). Examples of protecting groups will be found in the book: T. W. Greene et al., *Protective Groups in Organic Synthesis*, third edition, 1999, Wiley-Interscience or in: J. F. W. McOmie in *Protective Groups in Organic Chemistry*, Plenum Press, 1973. Examples of preferred protecting groups that may be mentioned are tert-butyloxycarbonyl (BOC) and 1-ethoxyethyl.

When PG denotes tert-butyloxycarbonyl, step 1 may be performed with di-tert-butyl dicarbonate in the presence of a base (such as triethylamine or pyridine) and optionally in the presence of N,N-dimethylaminopyridine, in an inert solvent (for example dichloromethane) or in the organic base itself at a temperature of between −10° C. and the boiling point of the reaction medium. When PG denotes 1-ethoxyethyl, step 1 may be performed with ethyl vinyl ether, in the presence of a catalytic amount of an acid such as hydrochloric acid, in an inert solvent such as toluene at a temperature of between 20° C. and the boiling point of the reaction medium.

Step 2

The acylation reaction of step 2 is performed with an acylating agent that allows the introduction of $R_6$. This agent may be, for example:
- an acid chloride $R_6C(O)Cl$. The reaction is then preferably performed in the presence of a base, for instance triethylamine, pyridine, diisopropylethylamine, potassium carbonate or sodium carbonate. The reaction may be performed in an inert solvent (for example dimethylformamide or tetrahydrofuran) or in the organic base itself at a temperature of between 0° C. and the boiling point of the reaction medium (G. Daidone et al, *Heterocycles*, 1996, 43 (11), 2385);
- an anhydride $(R_6CO)_2O$. The reaction is performed in an inert solvent (for example dimethylformamide, tetrahydrofuran or dichloromethane) or in the anhydride itself at a temperature of between 0° C. and the boiling point of the reaction medium (F. Albericio, *Synth. Commun.*, 2001, 31 (2), 225, G. Procter, *Tetrahedron*, 1995, 51 (47), 12837);
- an acid $R_6C(O)OH$. The reaction is preferably performed in the presence of an activating agent such as O-(7-azabenzotriazol-1-yl)-N,N,N',N'-tetramethyluronium hexafluorophosphate (ATUH) in the presence of a base (for example pyridine, diisopropylethylamine or triethylamine) in an inert solvent (for example dimethylformamide) at a temperature of between 0° C. and the boiling point of the reaction medium, or according to the well-known coupling methods of peptide chemistry (M. Bodanszky et al., *Principles of Peptide Synthesis*, Springer-Verleg, New York, N.Y., 1984, 9-58) or amide formation methods.

Step 3

Compound (Ia) is finally obtained after a deprotection step (step 3). When PG denotes tert-butyloxycarbonyl, step 3 may be performed in the presence of iodotrimethylsilane, or in acidic medium (for example trifluoroacetic acid, or hydrochloric acid in solvent such as ethanol, dichloromethane or dioxane) at a temperature of between 0° C. and the boiling point of the reaction medium, or alternatively in basic medium (potassium carbonate in a solvent such as an alcohol (preferably methanol) at a temperature of between 0° C. and the boiling point of the reaction medium and optionally with microwave irradiation), or in neutral medium in a solvent such as an alcohol (preferably methanol) with microwave irradiation. When PG denotes the 1-ethoxyethyl group, step 3 may be performed in the presence of a mineral acid such as hydrochloric acid, in a solvent such as tetrahydrofuran or water, at a temperature of between 20° C. and the boiling point of the reaction medium, or according to the well-known methods for deprotecting an amine function (T. W. Greene et al.).

After step (3), the compounds of formula (I) are isolated and may be purified by the usual known methods, for example by crystallization, chromatography or extraction.

The subject of the invention is thus also the process for preparing a compound of formula (Ib) below from a compound of formula (II):

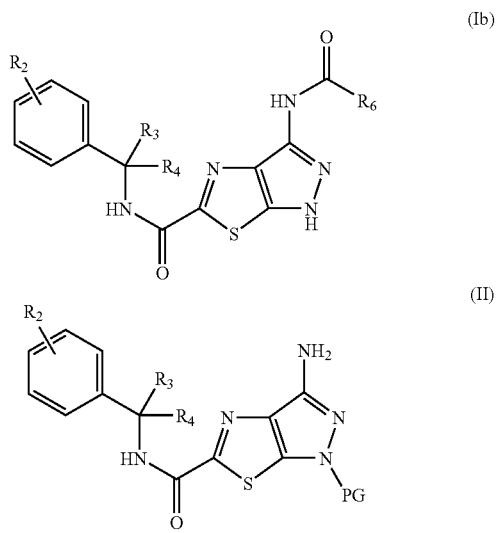

in which $R_2$, $R_3$, $R_4$ and $R_6$ have the same meanings as described above and PG denotes a protecting group for the NH function of the thiazole, and comprising, in order, the following steps:
- the acylation of the compound of formula (II) with an acylating agent, allowing the introduction of $R_6CO$ (step 2);
- the deprotection of the compound obtained from the preceding step (step 3).

Step 2 is preceded by a step of protecting the NH function of the compound of formula (Ia) with the protecting group PG (step 1).

Preparation of the Compounds of Formula (Ia)

The compounds of general formula (Ia) may be prepared from 2-trimethylsilylthiazole, according to Scheme 2:

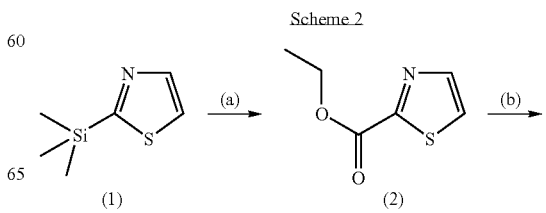

Scheme 2

-continued

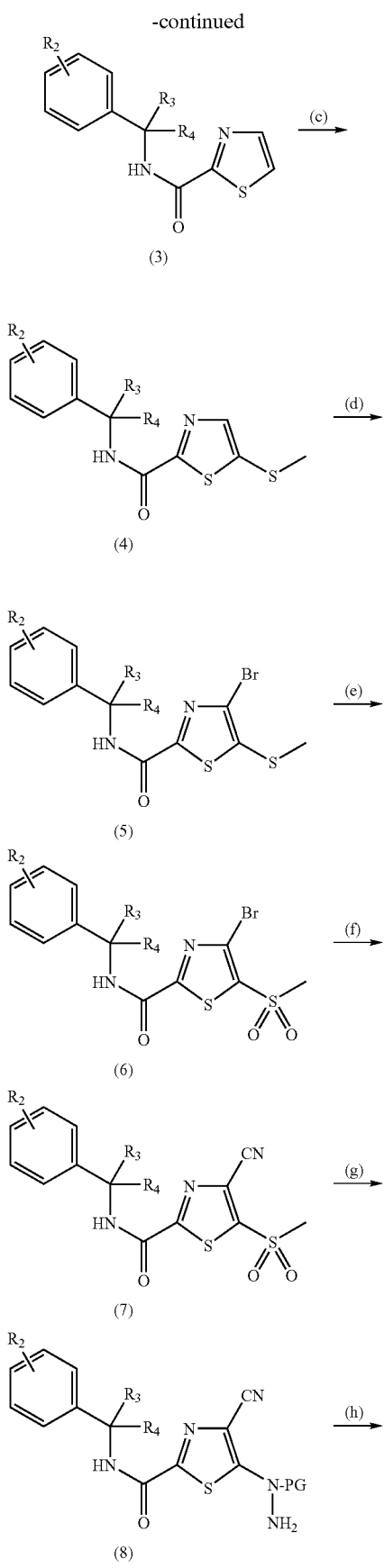

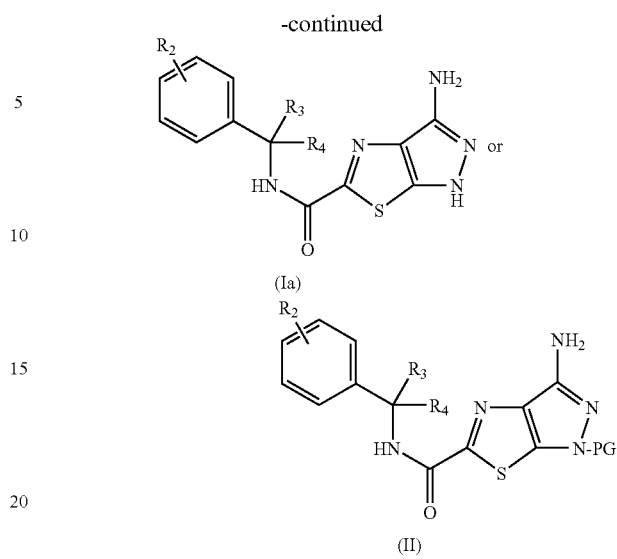

Reaction (a) may be performed in the presence of ethyl chloroformate, in an inert solvent such as toluene at a temperature of between 0° C. and the boiling point of the reaction medium, by adaptation of the method described in *J. Org. Chem.* 1988, 53, 1748.

The amidation reaction (b) may be performed in the presence of the amine of formula $(R_2)Ph\text{-}C(R_3)(R_4)\text{---}NH_2$ and of trimethylaluminium in a solvent such as toluene or dimethylformamide at a temperature of between 0° C. and the boiling point of the reaction medium.

Reaction (c) may be performed in the presence of a base such as an alkyllithium (preferably n-butyllithium) and dimethyl sulfide, in an inert solvent such as an ether (preferably tetrahydrofuran) at a temperature of between −78° C. and 0° C.

The bromination reaction (d) may be performed in the presence of a brominating agent such as N-bromosuccinimide, in an inert solvent such as chloroform at a temperature of between 20° C. and the boiling point of the reaction medium.

The oxidation reaction (e) may be performed in the presence of OXONE® (potassium peroxymonosulfate) or 3-chloroperoxybenzoic acid, in an inert solvent such as, respectively, tetrahydrofuran or dimethylformamide in the first case, or dichloromethane in the second case, at a temperature of between −20° C. and room temperature.

Reaction (f) may be performed in the presence of a cyanide derivative such as zinc cyanide, a palladium(0) derivative such as tris(dibenzylideneacetone)dipalladium(0) and a ligand such as 1,1'-bis(diphenylphosphino)ferrocene, in an inert solvent such as dimethylformamide at a temperature of between 20° C. and the boiling point of the reaction medium.

When PG represents a tert-butyloxycarbonyl group, reaction (g) may be performed in the presence of N-(tert-butyloxycarbonyl)hydrazine and a base such as potassium carbonate, in an inert solvent such as dimethylformamide at a temperature of between 20° C. and the boiling point of the reaction medium.

The cyclization reaction (h) may be performed in the presence of a mineral acid such as hydrochloric acid (preferably dry hydrochloric acid in dioxane) or sulfuric acid, in an inert solvent such as an alcohol (preferably ethanol) at a temperature of between 20° C. and the boiling point of the reaction medium. Reaction (h) finally leads to compound (Ia) or directly to compound (II) used in Scheme 1 (in which case step 1 of Scheme 1 is no longer necessary). One or other of the compounds is obtained depending on the operating conditions. For example, when PG represents a tert-butyloxycarbonyl group (preferred protecting group for Scheme 2), it is found that (Ia) or (II) is obtained depending on the duration of the cyclization reaction (h).

The intermediate compounds (3), (4), (5), (6), (7) and (8) also form part of the invention.

Variant of the Process of Scheme 1

For certain groups of compounds detailed below, a variant of the process described in Scheme 1 may be used, based on the use of the intermediate compounds (IIIa) or (IIIb) and of a step (a) before step (3):

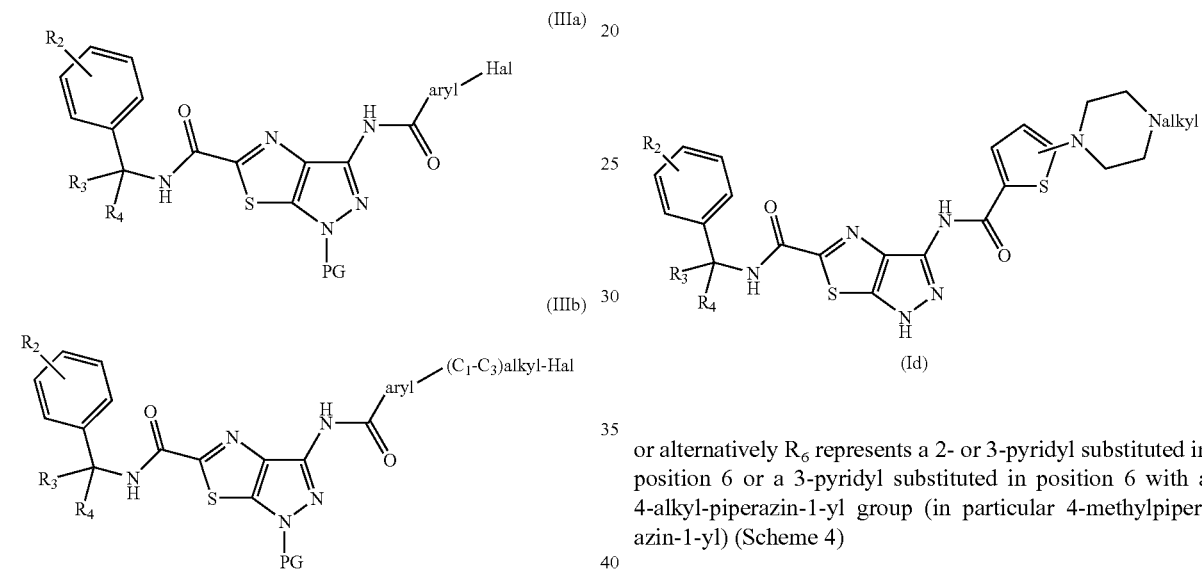

Hal represents a halogen atom linked to an aryl group or to a $(C_1-C_3)$alkyl group serving as a leaving group and possibly being a chlorine, bromine or fluorine atom. Compounds (IIIa) or (IIIb) may be prepared according to the process of Scheme 1.

When $R_6$ represents a 2-thienyl substituted in position 4 or 5 with a 4-alkylpiperazin-1-yl group (in particular 4-methylpiperazin-1-yl) (Scheme 3)

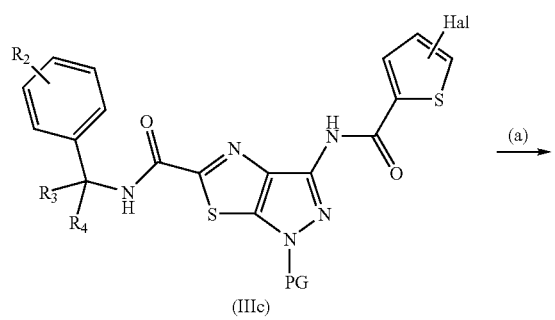

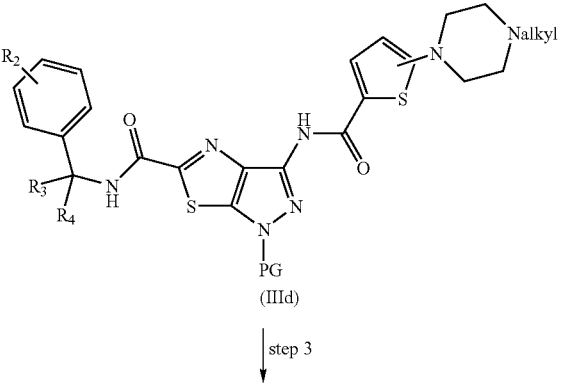

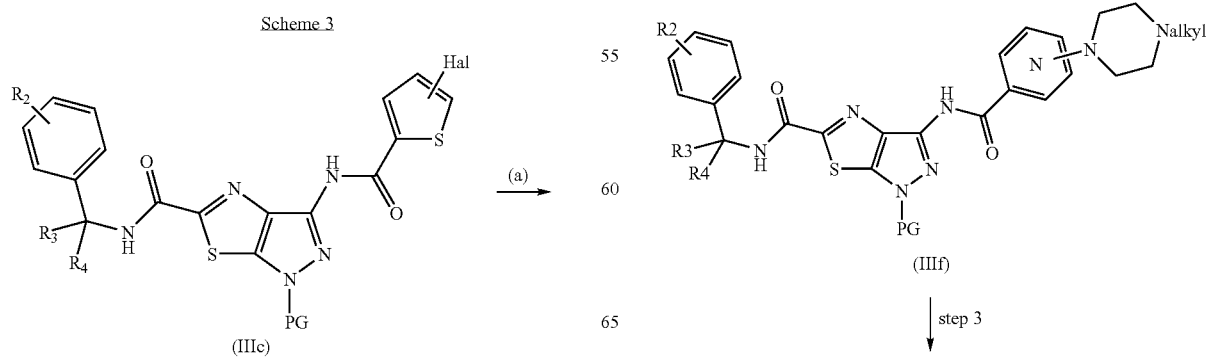

or alternatively $R_6$ represents a 2- or 3-pyridyl substituted in position 6 or a 3-pyridyl substituted in position 6 with a 4-alkyl-piperazin-1-yl group (in particular 4-methylpiperazin-1-yl) (Scheme 4)

Scheme 4

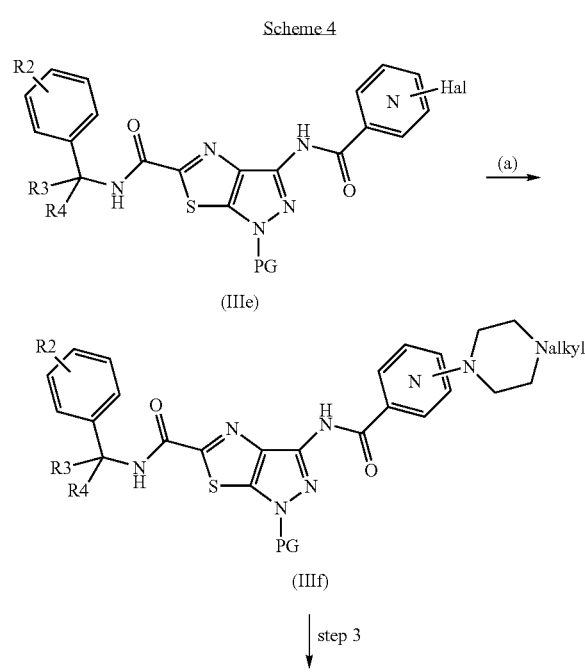

-continued

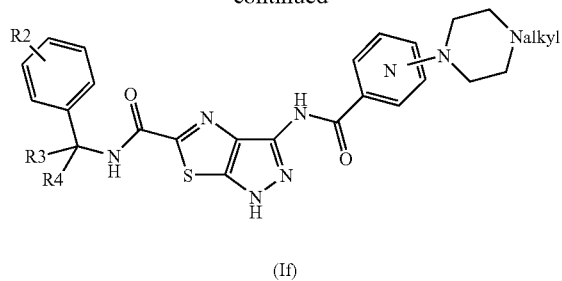

(If)

Reaction (a) may be performed:

when Hal represents a chlorine or bromine atom, using 4-methylpiperazine, in the presence of copper(I) iodide, an amine such as an amino acid (for example L-proline) or trans-1,2-diaminocyclohexane, or alternatively a diol, and a base such as potassium carbonate, tripotassium phosphate or caesium carbonate. An inert solvent such as dioxane, dimethyl sulfoxide or isopropanol is used, at a temperature of between 20° C. and the boiling point of the reaction medium, optionally with microwave irradiation according to the general methods described by D. Ma et al., *Synthesis* 2005, 496; *Org. Letters* 2003, 5, 2453 and by S. L. Buchwald et al., *Org. Letters* 2002, 4, 581;

when Hal represents a chlorine or bromine atom, using 4-methylpiperazine, in the presence of a palladium(0) derivative (for example tris(dibenzylideneacetone)dipalladium (0)), a ligand such as a phosphine derivative (for example 2-dicyclohexylphosphino-2'-(N,N-dimethylamino)biphenyl or 2-(di-t-butylphosphino)biphenyl), and a base, such as sodium tert-butoxide, tripotassium phosphate or caesium carbonate. An inert solvent such as toluene or dimethoxyethane is used, at a temperature of between 20° C. and the boiling point of the reaction medium, optionally with microwave irradiation, according to the general methods described by S. L Buchwald et al., *J. Org. Chem.* 2000, 65, 1158; *J. Org. Chem.* 2000, 65, 1144; *Org. Letters* 2003, 5, 2413 and by J. G. Verkade et al., *J. Org. Chem.* 2003, 68, 8416;

when Hal represents a chlorine or fluorine atom, using 4-methylpiperazine, in the presence of a base such as potassium carbonate and optionally in the presence of a complexing agent such as a crown ether (preferably 18-crown-6). An inert solvent such as dimethylformamide is used, at a temperature of between 20° C. and the boiling point of the reaction medium.

When $R_6$ represents

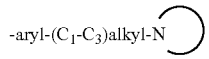

or a phenyl substituted with a —$(C_1$-$C_3)$alkyl-$NR_9R_{10}$ group:

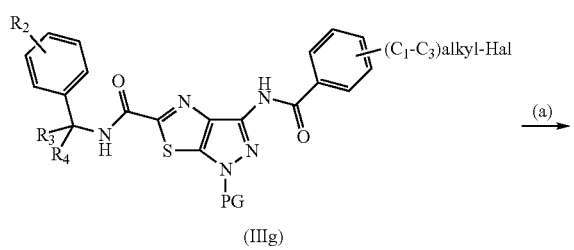

(IIIg)

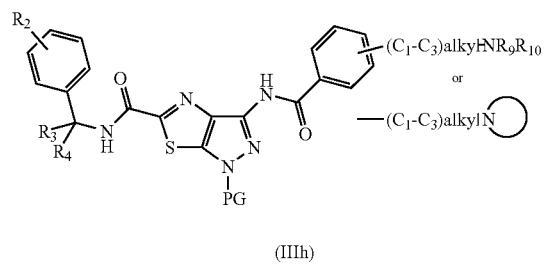

(IIIh)

↓ step 3

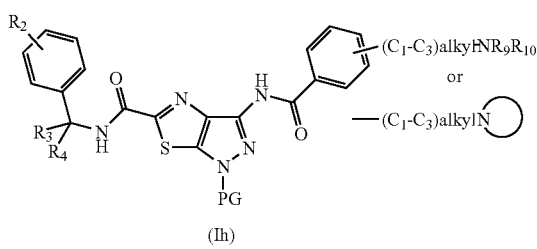

(Ih)

Reaction (a) may be performed in the presence of an amine of the type $HNR_9R_{10}$ or

in the presence of a salt such as tetrabutylammonium iodide in an inert solvent such as dimethylformamide, at a temperature of between 20° C. and the boiling point of the reaction medium.

A subject of the invention is thus also a process for preparing compounds (IIIb) from compounds (IIIa), comprising the following step:

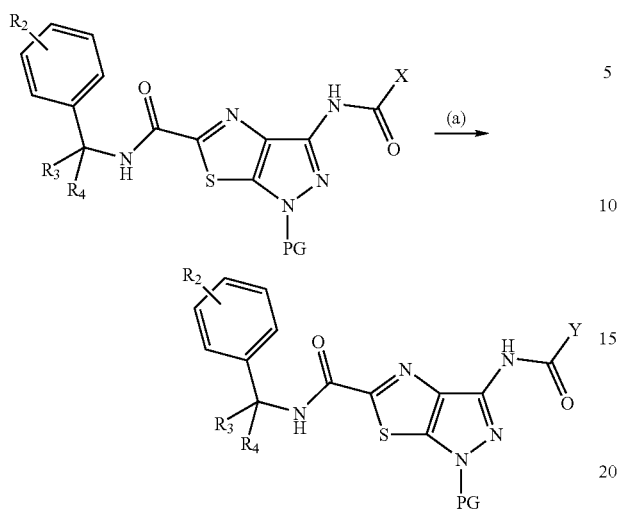

(a)

in which:

X represents

and Y represents

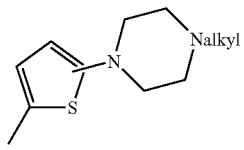

or
X represents

and Y represents

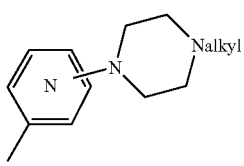

or alternatively

X represents

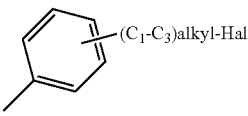

and Y represents

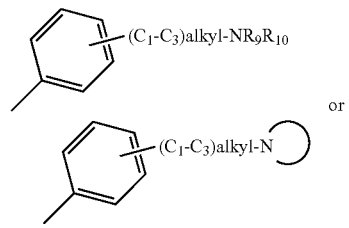

After step (a), the deprotection step 3 is applied.
The following compounds also form part of the invention:

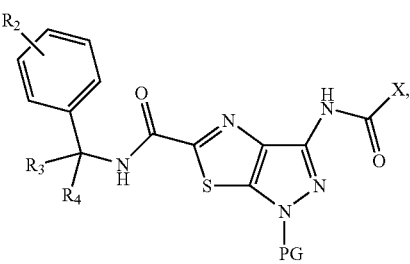

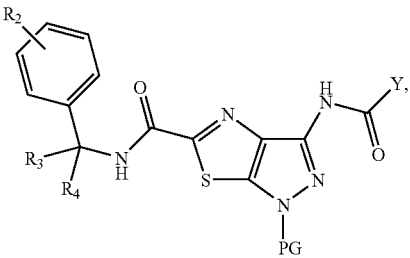

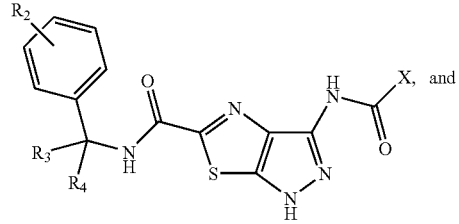

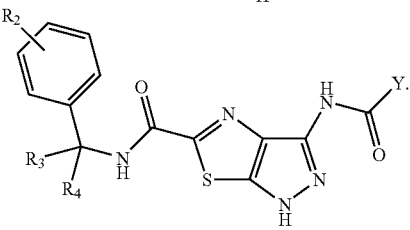

It is understood by those skilled in the art that, to perform the processes according to the invention described above, it may be necessary to introduce in addition to PG one or more other protecting group(s) for protecting one or more other chemical group(s), which is (are) subsequently eliminated.

EXAMPLES

The invention is also described by the examples that follow, which are given as illustrations of the invention.

Characterization Methods:

LC/MS Analyses Method A

The LC/MS analyses were performed on an HPLC machine equipped with Shimadzu model LC-10AD pumps, a Gilson model 215 sample changer and a Shimadzu model SPD-10A UV detector. The MS spectra were acquired in electrospray mode ($ES^+/ES^-$) on a PE Sciex API 100LC machine. The separation was performed on a YMC basic S5 column eluting with a gradient of acetonitrile containing 0.1% (v/v) of trifluoroacetic acid in water at a flow rate of 0.1 ml/minute. The data were analysed using the Micromass MassLynx software. The main ions observed are described.

LC/MS Analyses Method B

The LC/MS analyses were performed on an Agilent model HP1100 HPLC machine. The MS spectra were acquired in electrospray mode ($ES^+/ES^-$) on a Waters model ZQ machine. The separation was performed on a Waters Xbridge C18 column (3×50 mm, porosity 2.5 µm) maintained at a temperature of 60° C., eluting with a gradient of acetonitrile in water containing 0.1% (v/v) of formic acid at a flow rate of 1.1 ml/minute. The gradient has the following profile: 5% to 100% acetonitrile over 5 minutes, 100% acetonitrile constant for 0.5 minute, then return to 5% acetonitrile over 1 minute. The total analysis time, including the column re-equilibration period, is 7 minutes. The product abundance was measured using a diode array detector over a wavelength range from 210 to 400 nm and a Sedere Sedex 85 light scattering detector. The mass spectra were acquired over a range of 100 to 1200 atomic mass units. The data were analysed using the Micromass MassLynx software. The main ions observed are described.

LC/MS Analyses Method C

The LC/MS analyses were performed on an Agilent model HP1100 HPLC machine. The MS spectra were acquired in electrospray mode ($ES^+/ES^-$) on a Waters model ZQ machine. The separation was performed on a Waters Xbridge C18 column (3×50 mm, porosity 2.5 µm) maintained at a temperature of 70° C., eluting with a gradient of acetonitrile in water containing 0.1% (v/v) of formic acid, at a flow rate of 0.9 ml/minute. The gradient has the following profile: 5% to 100% acetonitrile over 5 minutes 30 seconds, 100% acetonitrile constant for 20 seconds, then return to 5% acetonitrile over 40 seconds. The total analysis time, including the column re-equilibration period, is 7 minutes. The product abundance was measured using a diode array detector over a wavelength range from 210 to 400 nm and a Sedere Sedex 85 light-scattering detector. The mass spectra were acquired over a range from 100 to 1200 atomic mass units. The data were analysed using the Micromass MassLynx software. The main ions observed are described.

LC/MS Analyses, Method D

The LC/MS analyses were performed on a Waters model Acquity UPLC HPLC machine. The MS spectra were acquired in electrospray mode ($ES^+/ES^-$) on a Waters model ZQ machine. The separation was performed on a Waters UPLC BeH C18 column (2.1×50 mm, porosity 1.7 µm) maintained at a temperature of 55° C., eluting with a gradient of acetonitrile in water containing 0.1% (v/v) of formic acid, at a flow rate of 1.2 ml/minute. The gradient has the following profile: 5% to 100% acetonitrile over 3 minutes, then return to 5% acetonitrile over 1 minute. The total analysis time, including the column re-equilibration period, is 4.5 minutes.

The product abundance was measured using a diode array detector over a wavelength range from 210 to 400 nm. The mass spectra were acquired over a range from 100 to 1200 atomic mass units. The data were analysed using the Micromass MassLynx software. The main ions observed are described.

$^1$H NMR Analyses

The analyses were performed at 400 MHz on a Bruker Avance DRX-400 spectrometer with the chemical shifts (δ in ppm) measured in dimethyl sulfoxide-$d_6$ (DMSO-$d_6$) referenced to 2.50 ppm at a temperature of 303 K.

Example 1

N-(1-Methyl-1-phenylethyl)(3-amino-1H-pyrazolo[4,3-d]thiazole)-5-carboxamide ($R_1$=$NH_2$, $R_5$=H, $R_3$=$R_4$=Me, $R_2$=H)

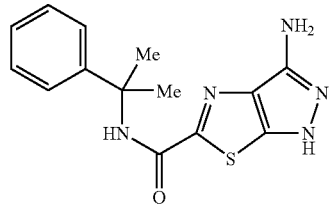

1.1 Ethyl 2-thiazolecarboxylate (2)

10 g (63.7 mmol) of 2-trimethylsilylthiazole (1) and 435 ml of toluene are placed in a 2-liter round-bottomed flask under argon. The reaction mixture is stirred and cooled using an ice bath, and, when the temperature has reached about 8° C., a solution of 12.2 ml (0.128 mol) of ethyl chloroformate in 500 ml of toluene is added. Once all the solution has been added, the mixture is left for about 10 minutes and then warmed to 25° C. After stirring for 20 hours, 200 ml of aqueous sodium carbonate solution are added and the mixture is stirred for 30 minutes. After separation of the phases by settling, the organic phase is washed with 200 ml of saturated aqueous sodium chloride solution. After drying over magnesium sulfate, the organic phase is concentrated to dryness under reduced pressure. The residue is purified by flash chromatography ($m_{silica}$=200 g; eluent: 60/40 cyclohexane/ethyl acetate). 5.12 g of ethyl 2-thiazolecarboxylate (2) are thus obtained in the form of a greenish liquid that crystallizes. $R_f$(50/50 cyclohexane/ethyl acetate)=0.52.

1.2 N-(1-Methyl-1-phenylethyl)thiazole-2-carboxamide 7.13 ml (50.0 mmol) of cumylamine and 156 ml of toluene are placed in a 1-liter three-necked flask with stirring and under an inert atmosphere. 24.8 ml (49.6 mmol) of trimethylaluminium are then added dropwise, and white fumes are evolved. After waiting until the medium has clarified, a solution of 3.9 g (24.8 mmol) of ethyl 2-thiazolecarboxylate (2) in 195 ml of toluene is added. The mixture is stirred for 15 minutes and then refluxed. After heating for 15 hours, the reaction medium is poured into 300 ml of 1M citric acid solution diluted with 200 ml of water and the whole is filtered through Celite®. The Celite® is washed with 100 ml of ethyl acetate and the aqueous phase is extracted with twice 100 ml of ethyl acetate. The organic extracts are combined and dried over magnesium sulfate, and after evaporating under reduced pressure, the residue is purified by flash chromatography ($m_{silica}$=200 g; eluent: dichloromethane). 4.1 g of N-(1-methyl-1-phenylethyl)thiazole-2-carboxamide are obtained in the form of a brick-red solid. $R_f$(dichloromethane)=0.4.

1.3 N-(1-Methyl-1-phenylethyl)(5-methylsulfanylthiazole)-2-carboxamide

A solution of 6.1 g (24.8 mmol) of N-(1-methyl-1-phenylethyl)thiazole-2-carboxamide in 60 ml of anhydrous tetrahydrofuran predried over molecular sieves is placed in a 250 ml three-necked flask under argon. After cooling to −78° C. with stirring, 31 ml (49.6 mmol) of n-butyllithium are added cautiously by syringe. A dark brown precipitate forms immediately. The mixture is stirred for 2 hours at −78° C., 4.4 ml (49.6 mmol) of dimethyl disulfide are then added and, after stirring for 1 hour at −78° C., the temperature is allowed to return to 25° C. and the mixture is stirred for one hour at this temperature. The reaction medium is then poured into 200 ml of water. The aqueous phase is extracted with 3 times 100 ml of ethyl acetate. The organic extracts are combined, dried over magnesium sulfate and then concentrated to dryness under reduced pressure. The residue is purified by flash chromatography ($m_{silica}$=200 g; eluent: 75/25 cyclohexane/ethyl acetate). 5.2 g of N-(1-methyl-1-phenylethyl)(5-methylsulfanylthiazole)-2-carboxamide are thus obtained in the form of a yellow solid that crystallizes. M.p.$_K$=68° C.

1.4 N-(1-Methyl-1-phenylethyl)(4-bromo-5-methylsulfanylthiazole)-2-carboxamide 5.2 g (17.8 mmol) of N-(1-methyl-1-phenylethyl)(5-methylsulfanylthiazole)-2-carboxamide are dissolved in 50 ml of chloroform in a 250 ml three-necked flask under argon. 3.49 g (19.6 mmol, 1.1 eq) of N-bromosuccinimide are added and the reaction mixture is stirred for 7 hours. The reaction mixture is then washed with 3 times 50 ml of water and the organic phase is then dried over magnesium sulfate and concentrated to dryness under reduced pressure. The residue is purified by flash chromatography ($m_{silica}$=200 g; eluent: 80/20 cyclohexane/ethyl acetate). 6.5 g of N-(1-methyl-1-phenylethyl)(4-bromo-5-methylsulfanylthiazole)-2-carboxamide are thus obtained in the form of a yellowish oil. $R_f$(50/50 ethyl acetate/cyclohexane)=0.88.

1.5 N-(1-Methyl-1-phenylethyl)(4-bromo-5-methanesulfonylthiazole)-2-carboxamide 6.5 g (0.018 mol) of N-(1-methyl-1-phenylethyl)(4-bromo-5-methylsulfanylthiazole)-2-carboxamide are dissolved in 250 ml of dimethylformamide in a 500 ml three-necked flask under argon. The solution is cooled in a water bath and 43 g (0.07 mol, 4 eq) of Oxone® (potassium peroxymonosulfate) are then added gradually by spatula. At the end of the addition, the bath is removed and the reaction mixture is stirred under argon for 15 h at 25° C. A further 11 g (0.018 mol, 1 eq) of Oxone® are then added and stirring is continued for 15 hours at 25° C. A further 11 g (0.018 mol, 1 eq) of Oxone® are added and stirring is continued for 15 hours at 25° C. The reaction medium is then poured into 300 ml of water and extracted with 4 times 150 ml of ethyl acetate. After drying over magnesium sulfate, the combined organic extracts are concentrated to dryness under reduced pressure. The residue is taken up in 400 ml of ethyl acetate and washed with 3 times 100 ml of water. After drying over magnesium sulfate, the organic phase is concentrated to dryness under reduced pressure. 6.7 g of N-(1-methyl-1-phenylethyl)(4-bromo-5-methanesulfonylthiazole)-2-carboxamide are thus obtained in the form of a cream-coloured solid. m.p.$_K$=146° C.

1.6 N-(1-Methyl-1-phenylethyl)(4-cyano-5-methanesulfonylthiazole)-2-carboxamide 4.5 g (11.2 mmol) of N-(1-methyl-1-phenylethyl)(4-bromo-5-methanesulfonylthiazole)-2-carboxamide are dissolved in 60 ml of dimethylformamide in a 250 ml three-necked flask under argon and with stirring. 1.3 g (11.1 mmol) of zinc cyanide, 1.24 g (2.24 mmol) of 1,1'-bis(diphenylphosphino)ferrocene (dppf) and 1.13 g (1.23 mmol) of tris(dibenzylideneacetone)dipalladium(0) ($Pd_2(dba)_3$) are then added. The mixture is degassed under argon with a Teflon tube dipping into the solution, for 2 minutes, the tube is then raised above the solution and the reaction mixture is heated at 120° C. for 15 hours while continuing the flushing with argon. The reaction medium is then poured into 200 ml of water and extracted with 200 ml of ethyl acetate. The extracts are filtered through Celite® and the aqueous phase is extracted with twice 100 ml of ethyl acetate. The organic extracts are combined, dried over magnesium sulfate and then concentrated to dryness under reduced pressure. The residue is taken up in 300 ml of dichloromethane and washed with 5 times 30 ml of water. After drying over magnesium sulfate, the organic phase is concentrated to dryness under reduced pressure. The residue is purified by flash chromatography ($m_{silica}$=100 g; eluent: 98/2 dichloromethane/methanol). 3.31 g of N-(1-methyl-1-phenylethyl)(4-cyano-5-methanesulfonylthiazole)-2-carboxamide are thus obtained in the form of a beige-coloured solid. m.p.$_K$=209° C.

1.7 N-(tert-Butyloxycarbonyl)-N-[4-cyano-2-(1-methyl-1-phenylethylcarbamoyl)thiazol-5-yl]hydrazine 1.03 g (2.95 mmol) of N-(1-methyl-1-phenylethyl)(4-cyano-5-methanesulfonylthiazole)-2-carboxamide are dissolved in 40 ml of dimethylformamide in a 50 ml three-necked flask under argon. 0.407 g of potassium carbonate (2.95 mmol) and 0.42 g (3.18 mmol) of N-(tert-butyloxycarbonyl)hydrazine are then gradually added. After stirring for 15 hours at 40° C., the reaction medium is concentrated to dryness under reduced pressure (heating bath at 65° C. max). The residue is taken up in 40 ml of dichloromethane and 40 ml of water and the emulsion obtained is broken by addition of salt. The organic phase is separated out by settling of the phases, dried over magnesium sulfate and then concentrated to dryness under reduced pressure. The residue is taken up in 50 ml of dichloromethane and 30 ml of water. The emulsion obtained is broken by addition of salt. The organic phase is separated out after settling of the phases, dried over magnesium sulfate and then concentrated to dryness under reduced pressure. The residue is purified by flash chromatography ($m_{silica}$=50 g; eluent: 98/2 dichloromethane/methanol). 0.308 g of N-(tert-butyloxycarbonyl)-N-[4-cyano-2-(1-methyl-1-phenylethylcarbamoyl)thiazol-5-yl]hydrazine is thus obtained in the form of a yellow foam. m.p.$_K$=70° C.

1.8 N-(1-Methyl-1-phenylethyl)(3-amino-1H-pyrazolo[4,3-d]thiazole)-5-carboxamide 0.083 g (0.21 mmol) of N-(tert-butyloxycarbonyl)-N-[4-cyano-2-(1-methyl-1-phenylethylcarbamoyl)thiazol-5-yl]hydrazine is dissolved in 5 ml of ethanol in a 50 ml round-bottomed flask. 1 ml (4.0 mmol) of a 4M solution of hydrochloric acid in dioxane is then gradually added and the mixture is stirred for 15 hours at 25° C. The reaction medium is then concentrated to dryness under reduced pressure (40° C.) and the residue is taken up into 20 ml of dichloromethane and 20 ml of water. The aqueous phase is basified with 0.1N sodium hydroxide solution. After separation of the phases by settling, the organic phase is dried over magnesium sulfate and concentrated to dryness under reduced pressure. The residue is purified by flash chromatography ($m_{silica}$=30 g; eluent: 90/10 dichloromethane/methanol). 28 mg of N-(1-methyl-1-phenylethyl)(3-amino-1H-pyrazolo[4,3-d]thiazole)-5-carboxamide are thus obtained in the form of a yellow foam. m.p.$_K$=110° C. $R_f$(90/10 dichloromethane/methanol)=0.48. $^1$H NMR (400 MHz, DMSO-d$_6$): 6 ppm 1.70 (s, 6H); 6.17 (broad m, 2H); 7.21 (t, J=7.5 Hz, 1H); 7.32 (t, J=7.5 Hz, 2H); 7.42 (broad d, J=7.5 Hz, 2H); 8.10 (broad m, 1H); 12.2 (broad m, 1H).

Example 2

N-(1-Methyl-1-phenylethyl)-3-[4-(4-methylpiperazin-1-yl)benzoylamino]-1H-pyrazolo[4,3-d]thiazole-5-carboxamide

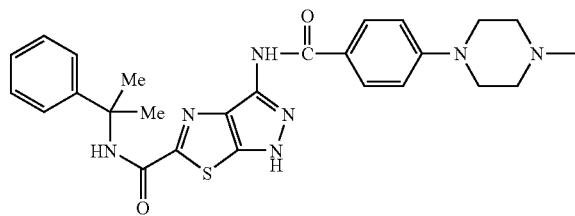

2.1 tert-Butyl 3-amino-5-(1-methyl-1-phenylethylcarbamoyl)-1H-pyrazolo[4,3-d]thiazole-1-carboxylate 0.115 g (0.38 mmol) of N-(1-methyl-1-phenylethyl)(3-amino-1H-pyrazolo[4,3-d]thiazole)-5-carboxamide are dissolved in 5 ml of pyridine in a 100 ml round-bottomed flask. 0.092 g (0.42 mmol) of di-tert-butyl dicarbonate is then gradually added and the reaction mixture is stirred for 15 hours at 25° C. The reaction mixture is then concentrated to dryness under reduced pressure (40° C.) and the residue is taken up in 40 ml of ethyl acetate and washed with 3 times 20 ml of water. The organic phase is dried over magnesium sulfate and then concentrated to dryness under reduced pressure. 0.144 g of tert-butyl 3-amino-5-(1-methyl-1-phenylethylcarbamoyl)-1H-pyrazolo[4,3-d]thiazole-1-carboxylate is thus obtained in the form of a yellow foam. LC-MS-DAD-ELSD: $t_R$=4.7 min, m/z=402.

2.2 tert-Butyl 5-(1-methyl-1-phenylethylcarbamoyl)-3-[4-(4-methylpiperazin-1-yl)benzoylamino]-1H-pyrazolo[4,3-d]thiazole-1-carboxylate 2.0 g (5.0 mmol) of tert-butyl 3-amino-5-(1-methyl-1-phenylethylcarbamoyl)-1H-pyrazolo[4,3-d]thiazole-1-carboxylate dissolved in 40 ml of pyridine are placed in a 250 ml round-bottomed flask under argon. 1.56 g (5.0 mmol) of 4-(4-methylpiperazin-1-yl)benzoyl chloride dihydrochloride (prepared according to WO 2005/113494) are then gradually added and the mixture is stirred for 15 hours at 25° C. The reaction medium is then concentrated to dryness under reduced pressure (40° C.) and the residue is taken up in 50 ml of dichloromethane and 50 ml of water, and basified with 0.1N sodium hydroxide solution. The emulsion obtained is resorbed by saturation with sodium chloride. After separation of the phases by settling, the organic phase is dried over magnesium sulfate and concentrated to dryness under reduced pressure. The residue is purified by flash chromatography ($m_{silica}$=30 g; eluent: 95/5 dichloromethane/methanol). 1.32 g of tert-butyl 5-(1-methyl-1-phenylethylcarbamoyl)-3-[4-(4-methylpiperazin-1-yl)benzoylamino]-1H-pyrazolo[4,3-d]thiazole-1-carboxylate are thus obtained in the form of a yellow foam. $^1$H NMR (400 MHz, DMSO-d$_6$): δ ppm 1.62 (s, 9H); 1.70 (s, 6H); 2.22 (s, 3H); 2.44 (m, 4H); 3.32 (m, 4H); 7.02 (d, J=8.5 Hz, 2H); 7.20 (t, J=7.5 Hz, 1H); 7.30 (t, J=7.5 Hz, 2H); 7.40 (d, J=7.5 Hz, 2H); 7.95 (d, J=8.5 Hz, 2H); 8.71 (s, 1H); 11.05 (s, 1H). LC-MS-DAD-ELSD: 602(−)=(M−H)(−); 604(+)=(M+H)(+).

2.3 N-(1-Methyl-1-phenylethyl)-3-[4-(4-methylpiperazin-1-yl)benzoylamino]-1H-pyrazolo[4,3-d]thiazole-5-carboxamide 2.47 g (4.1 mmol) of tert-butyl 5-(1-methyl-1-phenylethylcarbamoyl)-3-[4-(4-methylpiperazin-1-yl)benzoylamino]-1H-pyrazolo[4,3-d]thiazole-1-carboxylate dissolved in 120 ml of ethanol are placed in a 500 ml round-bottomed flask. 21 ml (84 mmol) of a 4M solution of hydrochloric acid in dioxane are then added dropwise and the reaction mixture is stirred for 15 hours at 25° C. A further 21 ml (84 mmol) of a 4M solution of hydrochloric acid in dioxane are then added and the mixture is stirred for 15 hours at 25° C. The reaction medium is then concentrated to dryness under reduced pressure (40° C.) and the residue is taken up in 500 ml of dichloromethane and 500 ml of water, and basified with 0.1N sodium hydroxide solution. The emulsion obtained is resorbed by saturation with sodium chloride. During the separation of the phases by settling, 1.27 g of an off-white solid are isolated by filtration, and are purified by flash chromatography ($m_{silica}$=30 g; eluent: 90/10 dichloromethane/methanol). 0.92 g of N-(1-methyl-1-phenylethyl)-3-[4-(4-methylpiperazin-1-yl)benzoylamino]-1H-pyrazolo[4,3-d]thiazole-5-carboxamide is thus obtained in the form of a yellow foam. After separation of the phases by settling, the organic phase is dried over magnesium sulfate and concentrated to dryness under reduced pressure (40° C.). The yellow residue is purified by flash chromatography ($m_{silica}$=30 g; eluent: 90/10 dichloromethane/methanol). 0.61 g of N-(1-methyl-1-phenylethyl)-3-[4-(4-methylpiperazin-1-yl)benzoylamino]-1H-pyrazolo[4,3-d]thiazole-5-carboxamide is thus obtained in the form of a yellow foam. The two batches are combined, triturated in 20 ml of diethyl ether, filtered and then dried under reduced pressure (40° C.). 1.45 g of N-(1-methyl-1-phenylethyl)-3-[4-(4-methylpiperazin-1-yl)benzoylamino]-1H-pyrazolo[4,3-d]thiazole-5-carboxamide are thus obtained in the form of a yellow solid. m.p.$_K$=264° C. $^1$H NMR (400 MHz, DMSO-$d_6$): δ ppm 1.71 (s, 6H); 2.22 (s, 3H); 2.45 (m, 4H); 3.32 (m, 4H); 7.02 (d, J=8.5 Hz, 2H); 7.20 (t, J=7.5 Hz, 1H); 7.31 (t, J=7.5 Hz, 2H); 7.41 (d, J=7.5 Hz, 2H); 7.97 (d, J=8.5 Hz, 2H); 8.49 (broad s, 1H); 10.8 (broad m, 1H); 13.5 (broad m, 1H).

Example 3

N-(1-Methyl-1-phenylethyl)-3-(4-morpholin-4-yl-benzoylamino)-1H-pyrazolo[4,3-d]thiazole-5-carboxamide

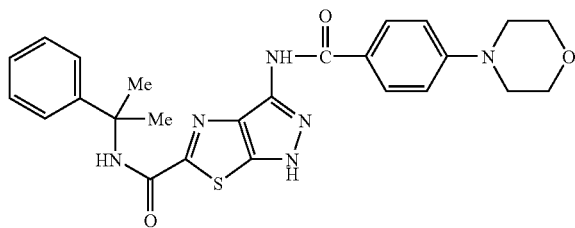

3.1 tert-Butyl 5-(1-methyl-1-phenylethylcarbamoyl)-3-(4-morpholin-4-ylbenzoylamino)-1H-pyrazolo[4,3-d]thiazole-1-carboxylate 0.40 g (0.998 mmol) of tert-butyl 3-amino-5-(1-methyl-1-phenylethylcarbamoyl)-1H-pyrazolo[4,3-d]thiazole-1-carboxylate dissolved in 10 ml of pyridine is placed in a 50 ml round-bottomed flask under argon. 0.25 g (0.996 mmol) of 4-(4-morpholinyl)benzoyl chloride dihydrochloride (prepared according to WO 95/04729) is then gradually added and the mixture is stirred for 15 hours at 25° C. The reaction medium is then concentrated to dryness under reduced pressure (40° C.) and the residue is taken up in 50 ml of dichloromethane and 50 ml of water, and basified with 0.1N sodium hydroxide solution. The emulsion obtained is resorbed by saturation with sodium chloride. After separation of the phases by settling, the organic phase is dried over magnesium sulfate and concentrated to dryness under reduced pressure. The residue is purified by flash chromatography ($m_{silica}$=30 g; eluent: 99/1 dichloromethane/methanol). 0.19 g of tert-butyl 5-(1-methyl-1-phenylethylcarbamoyl)-3-(4-morpholin-4-ylbenzoylamino)-1H-pyrazolo[4,3-d]thiazole-1-carboxylate is thus obtained in the form of a yellow foam. $^1$H NMR (400 MHz, DMSO-$d_6$): δ ppm 1.61 (s, 9H); 1.70 (s, 6H); 3.29 (masked m, 4H); 3.75 (m, 4H); 7.03 (d, J=8.5 Hz, 2H); 7.20 (t, J=7.5 Hz, 1H); 7.30 (t, J=7.5 Hz, 2H); 7.40 (d, J=7.5 Hz, 2H); 7.97 (d, J=8.5 Hz, 2H); 8.69 (s, 1H); 11.1 (broad m, 1H). LC-MS-DAD-ELSD: 591(+)=(M+H)(+); 535(+)=591(+)-tBu+H.

3.2 N-(1-Methyl-1-phenylethyl)-3-(4-morpholin-4-ylbenzoylamino)-1H-pyrazolo[4,3-d]thiazole-5-carboxamide 0.19 g (0.32 mmol) of tert-butyl 5-(1-methyl-1-phenylethylcarbamoyl)-3-(4-morpholin-4-ylbenzoylamino)-1H-pyrazolo[4,3-d]thiazole-1-carboxylate dissolved in 7 ml of ethanol is placed in a 50 ml round-bottomed flask. 1.6 ml (6.4 mmol) of a 4M solution of hydrochloric acid in dioxane are then added and the reaction mixture is stirred for 15 hours at 25° C. A further 1.6 ml (6.4 mmol) of a 4M solution of hydrochloric acid in dioxane are then added and the mixture is stirred for 15 hours at 25° C. The reaction medium is then concentrated to dryness under reduced pressure (40° C.) and the residue is taken up in 40 ml of dichloromethane and 40 ml of water, and basified with 0.1N sodium hydroxide solution. The emulsion obtained is resorbed by saturation with sodium chloride. After separation of the phases by settling, the organic phase is dried over magnesium sulfate and concentrated to dryness under reduced pressure (40° C.). The yellow residue is purified by flash chromatography ($m_{silica}$=30 g; eluent: 97/3 dichloromethane/methanol). 0.097 g of N-(1-methyl-1-phenylethyl)-3-(4-morpholin-4-ylbenzoylamino)-1H-pyrazolo[4,3-d]thiazole-5-carboxamide is thus obtained in the form of a yellow foam. m.p.$_K$=266° C. $^1$H NMR (400 MHz, DMSO-$d_6$): δ ppm 1.70 (s, 6H); 3.29 (masked m, 4H); 3.75 (m, 4H); 7.04 (d, J=8.5 Hz, 2H); 7.20 (t, J=7.5 Hz, 1H); 7.31 (t, J=7.5 Hz, 2H); 7.41 (d, J=7.5 Hz, 2H); 7.99 (d, J=8.5 Hz, 2H); 8.50 (broad s, 1H); 10.8 (broad m, 1H); 13.6 (broad m, 1H).

Example 4

N-(1-methyl-1-phenylethyl)-3-(4-methoxybenzoylamino)-1-H-pyrazolo[4,3-d]thiazole-5-carboxamide

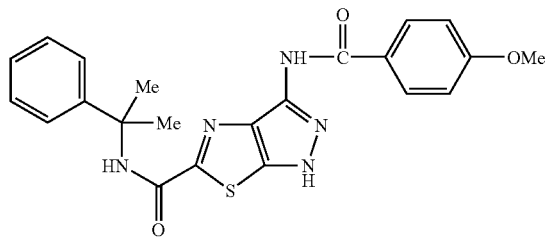

4.1 tert-Butyl 3-(4-methoxybenzoylamino)-5-(1-methyl-1-phenylethylcarbamoyl)-1H-pyrazolo[4,3-d]thiazole-1-carboxylate 0.20 g (0.50 mmol) of tert-butyl 3-amino-5-(1-methyl-1-phenylethylcarbamoyl)-1H-pyrazolo[4,3-d]thiazole-1-carboxylate dissolved in 5 ml of pyridine is placed in a 50 ml round-bottomed flask under argon. A solution of 0.09 g (0.53 mmol) of 4-methoxybenzoyl chloride (prepared according to J. Org. Chem. 1976, 41, 2566) in 2.0 ml of tetrahydrofuran is then added dropwise and the mixture is stirred for 15 hours at 25° C. The reaction medium is then concentrated to dryness under reduced pressure (40° C.) and the residue is taken up in 30 ml of dichloromethane and 30 ml of water, and basified with 0.1N sodium hydroxide solution. The emulsion obtained is resorbed by saturation with sodium chloride. After separation of the phases by settling, the organic phase is dried over magnesium sulfate and concentrated to dryness under reduced pressure. The residue is purified by flash chromatography ($m_{silica}$=30 g; eluent: 95/5 dichloromethane/methanol). 0.05 g of tert-butyl 3-(4-methoxy-benzoylamino)-5-(1-methyl-1-phenylethylcarbamoyl)-1H-pyrazolo[4,3-d]thiazole-1-carboxylate is thus obtained in the form of a cream-coloured foam. 0.16 g of an impure batch is also obtained, and is repurified by flash chromatography ($m_{silica}$=30 g; eluent: 95/5 dichloromethane/methanol). 0.04 g of tert-butyl 3-(4-methoxybenzoylamino)-5-(1-methyl-1-phenylethylcarbamoyl)-1H-pyrazolo[4,3-d]thiazole-1-carboxylate is thus obtained in the form of a cream-coloured foam. $^1$H NMR (400 MHz, DMSO-$d_6$): δ ppm 1.61 (s, 9H); 1.71 (s, 6H); 3.86 (s, 3H); 7.10 (d, J=8.5 Hz, 2H); 7.20 (t, J=7.5 Hz, 1H); 7.30 (t, J=7.5 Hz, 2H); 7.40 (d, J=7.5 Hz, 2H); 8.07 (d, J=8.5 Hz, 2H); 8.71 (s, 1H); 11.25 (broad s, 1H). LC-MS-DAD-ELSD: 534 (−)=(M−H)(−); 536(+)=(M+H)(+).

4.2 N-(1-Methyl-1-phenylethyl)-3-(4-methoxybenzoylamino)-1-H-pyrazolo[4,3-d]thiazole-5-carboxamide 0.16 g (0.31 mmol) of tert-butyl 3-(4-methoxybenzoylamino)-5-(1-methyl-1-phenylethylcarbamoyl)-1H-pyrazolo[4,3-d]thiazole-1-carboxylate dissolved in 7 ml of ethanol is placed in a 100 ml round-bottomed flask. 1.5 ml (6.0 mmol) of a 4M solution of hydrochloric acid in dioxane are then added and the reaction mixture is stirred for 15 hours at 25° C. A further 1.5 ml (6.0 mmol) of 4M solution of hydrochloric acid in dioxane are added and the mixture is stirred for 15 hours at 25° C. The reaction medium is then concentrated to dryness under reduced pressure (40° C.) and the residue is taken up in 30 ml of dichloromethane and 30 ml of water, and basified with 0.1N sodium hydroxide solution. The emulsion obtained is resorbed by saturation with sodium chloride. After separation of the phases by settling, the organic phase is dried over magnesium sulfate and concentrated to dryness under reduced pressure (40° C.). The residue is purified by flash chromatography ($m_{silica}$=30 g; eluent: 95/5 dichloromethane/methanol). 0.103 g of N-(1-methyl-1-phenylethyl)-3-(4-methoxybenzoylamino)-1-H-pyrazolo[4,3-d]thiazole-5-carboxamide is thus obtained in the form of a cream-coloured foam. m.p.$_K$=226° C. $^1$H NMR (400 MHz, DMSO-$d_6$): δ ppm 1.70 (s, 6H); 3.86 (s, 3H); 7.09 (d, J=8.5 Hz, 2H); 7.20 (t, J=7.5 Hz, 1H); 7.30 (t, J=7.5 Hz, 2H); 7.41 (d, J=7.5 Hz, 2H); 8.07 (d, J=8.5 Hz, 2H); 8.53 (broad s, 1H); from 10.0 to 15.0 (very broad m, 2H).

Example 5

N-(1-methyl-1-phenylethyl)-3-[(thiophene-3-carbonyl)amino]-1H-pyrazolo[4,3-d]thiazole-5-carboxamide

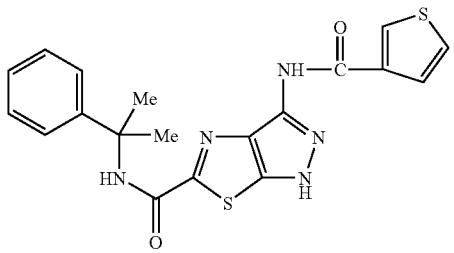

5.1 tert-Butyl 5-(1-methyl-1-phenylethylcarbamoyl)-3-[(thiophene-3-carbonyl)amino]-1H-pyrazolo[4,3-d]thiazole-1-carboxylate 0.20 g (0.50 mmol) of tert-butyl 3-amino-5-(1-methyl-1-phenylethylcarbamoyl)-1H-pyrazolo[4,3-d]thiazole-1-carboxylate dissolved in 5 ml of pyridine is placed in a 50 ml round-bottomed flask under argon. A solution of 0.07 g (0.50 mmol) of thiophene-3-carbonyl chloride (prepared according to FR 2 411 188) in 2.0 ml of tetrahydrofuran is then added dropwise and the mixture is stirred for 15 hours at 25° C. The reaction medium is then concentrated to dryness under reduced pressure (40° C.) and the residue is taken up in 30 ml of dichloromethane and 30 ml of water, and basified with 0.1N sodium hydroxide solution. The emulsion obtained is resorbed by saturation with sodium chloride. After separation of the phases by settling, the organic phase is dried over magnesium sulfate and concentrated to dryness under reduced pressure. The residue is purified by flash chromatography ($m_{silica}$=30 g; eluent: 95/5 dichloromethane/methanol). 0.074 g of tert-butyl 5-(1-methyl-1-phenylethylcarbamoyl)-3-[(thiophene-3-carbonyl)amino]-1H-pyrazolo[4,3-d]thiazole-1-carboxylate is thus obtained in the form of a cream-coloured foam. 0.14 g of an impure batch is also obtained, and is repurified by flash chromatography ($m_{silica}$=30 g; eluent: 95/5 dichloromethane/methanol). 0.013 g of tert-butyl 5-(1-methyl-1-phenylethylcarbamoyl)-3-[(thiophene-3-carbonyl)amino]-1H-pyrazolo[4,3-d]thiazole-1-carboxylate is thus obtained in the form of a cream-coloured foam, along with 0.11 g of an impure batch, which is repurified by flash chromatography ($m_{silica}$=30 g; eluent: 95/5 dichloromethane/methanol). 0.04 g of tert-butyl 5-(1-methyl-1-phenylethylcarbamoyl)-3-[(thiophene-3-carbonyl)amino]-1H-pyrazolo[4,3-d]thiazole-1-carboxylate is thus obtained in the form of a cream-coloured foam. $^1$H NMR (400 MHz, DMSO-$d_6$): δ ppm 1.62 (s, 9H); 1.71 (s, 6H); 7.20 (t, J=7.5 Hz, 1H); 7.30 (t, J=7.5 Hz, 2H); 7.41 (d, J=7.5 Hz, 2H); 7.70 (d, J=2.0 Hz, 2H); 8.50 (t, J=2.0 Hz, 1H); 8.70 (s, 1H); 11.25 (s, 1H). LC-MS-DAD-ELSD: 510(−)=(M−H)(−); 512(+)=(M+H)(+).

5.2 N-(1-Methyl-1-phenylethyl)-3-[(thiophene-3-carbonyl)amino]-1H-pyrazolo[4,3-d]thiazole-5-carboxamide 0.16 g (0.32 mmol) of tert-butyl 5-(1-methyl-1-phenylethylcarbamoyl)-3-[(thiophene-3-carbonyl)amino]-1H-pyrazolo[4,3-d]thiazole-1-carboxylate dissolved in 7 ml of ethanol is placed in a 100 ml round-bottomed flask. 1.6 ml (6.4 mmol) of a 4M solution of hydrochloric acid in dioxane are then added and the reaction mixture is stirred for 15 hours at 25° C. A further 1.6 ml (6.4 mmol) of 4M solution of hydrochloric acid in dioxane are then added and the mixture is stirred for 15 hours at 25° C. The reaction medium is then concentrated to dryness under reduced pressure (40° C.) and the residue is taken up in 30 ml of dichloromethane and 30 ml of water, and basified with 0.1N sodium hydroxide solution. The emulsion obtained is resorbed by saturation with sodium chloride. After separation of the phases by settling, the organic phase is dried over magnesium sulfate and concentrated to dryness under reduced pressure (40° C.). The residue is purified by flash chromatography ($m_{silica}$=30 g; eluent: 95/5 dichloromethane/methanol). 0.104 g of N-(1-methyl-1-phenylethyl)-3-[(thiophene-3-carbonyl)amino]-1H-pyrazolo[4,3-d]thiazole-5-carboxamide is thus obtained in the form of a cream-coloured foam. m.p.$_K$=221° C. $^1$H NMR (400 MHz, DMSO-$d_6$): δ ppm 1.70 (s, 6H); 7.20 (t, J=7.5 Hz, 1H); 7.31 (t, J=7.5 Hz, 2H); 7.41 (d, J=7.5 Hz, 2H); 7.69 (m, 2H); 8.46 (broad s, 1H); 8.53 (broad s, 1H); from 10.0 to 15.0 (very broad m, 2H).

Inhibitory Activity

Many proteins involved in chromosome segregation and spindle assembly have been identified in yeast and *drosophila*. Disorganization of these proteins leads to the non-segregation of the chromosomes and to monopolar or disorganized spindles. Among these proteins, certain kinases, including Aurora and Ipl1, originating, respectively, from *drosophila* and from *S. cerevisiae*, are necessary for chromosome segregation and separation of the centrosome. A human analogue of yeast Ipl1 has recently been cloned and characterized by various laboratories. This kinase, known as aurora2, STK15 or BTAK, belongs to the serine/threonine kinase family. Bischoff et al. have shown that Aurora2 is oncogenic, and is amplified in human colorectal cancers (EMBO J, 1998, 17, 3052-3065). This has also been illustrated in cancers involving epithelial tumors such as breast cancer.

Tie2 (TEK) is a member of a family of tyrosine kinase receptors, which is specific to endothelial cells. Tie2 is the first receptor with tyrosine kinase activity for which both the agonist (angiopoietin 1 or Ang1), which stimulates the autophosphorylation of the receptor and cell signalling [S. Davis et al. (1996) Cell 87, 1161-1169], and the antagonist (angiopoietin 2 or Ang2) [P. C. Maisonpierre et al. (1997) Science 277, 55-60] are known. Angiopoietin 1 can synergize with VEGF in the final stages of neoangiogenesis [Asahara T. Circ. Res. (1998) 233-240]. Knock-out experiments and transgenic manipulations of the expression of Tie2 or of Ang1 lead to animals that present vascularization defects [D. J. Dumont et al. (1994) Genes Dev. 8, 1897-1909 and C. Suri (1996) Cell 87, 1171-1180]. The binding of Ang1 to its receptor leads to autophosphorylation of the kinase domain of Tie2, which is essential for neovascularization and also for the recruitment and interaction of blood vessels with the pericytes and smooth muscle cells; these phenomena contribute towards the maturation and stability of the newly formed blood vessels [P. C. Maisonpierre et al. (1997) Science 277, 55-60]. Lin et al. (1997) J. Clin. Invest. 100, 8: 2072-2078 and Lin P. (1998) PNAS 95, 8829-8834 have shown an inhibition of tumour growth and vascularization, and also a reduction in lung metastases, during adenoviral infections or injections of the extracellular domain of Tie-2 (Tek) into models of melanoma and breast tumour xenografts. Tie2 inhibitors may be used in situations in which neovascularization takes place inappropriately (i.e. in diabetic retinopathy, chronic inflammation, psoriasis, Kaposi's sarcoma, chronic neovascularization due to macular degeneration, rheumatoid arthritis, infantile haemoangioma and cancers).

Determination of the Inhibition of the Kinases Aurora1 and Aurora2

The inhibitory effect of compounds with respect to the kinases Aurora1 and Aurora2 is determined by means of an enzymatic test using radioactivity detection. The kinase activity of Aurora1 and Aurora2 is evaluated via the phosphorylation of the substrate Numa-histidine in the presence of radio-labelled ATP ($[^{33}P]$ATP) using 96-well Flashplate plates in which the nickel chelate is bound to the surface of the microplate. The amount of $^{33}P$ phosphate incorporated into the NuMA substrate is proportional to the activity of the enzyme Aurora1 or Aurora2.

Aurora1: Aurora-B/INCENP-C3 recombinant complex, purified to about 50%, the N-terminal end of Aurora-B of which has been labelled with histidine.

Aurora2: whole recombinant protein comprising an N-terminal histidine tail, was expressed in E. coli and purified to more than 82%.

NuMA (nuclear protein that combines with the mitotic apparatus): 424-amino acid fragment, expressed in E. coli, the N-terminal end of which has been labelled with histidine, and used as substrate for the two Aurora enzymes.

The microplates used are 96-well Flash-Plate plates, nickel chelate (Perkin-Elmer, model SMP107). The products to be evaluated are incubated in a reaction volume of 100 μL per well, in the presence of 10 nM of Aurora1 or Aurora2, 500 nM of NuMA substrate in a buffer composed of 50 mM Tris/HCl (pH 7.5), 50 mM NaCl, 5 mM $MgCl_2$ (Aurora-B) or 10 mM $MgCl_2$ (Aurora-A) and 1 mM DTT, at 37° C. 80 μL of enzyme/substrate incubation buffer are distributed in each well, followed by 10 μL of product to be evaluated, at variable concentrations. The reaction is initiated by adding 1 μM final of ATP containing 0.2 μCi of $[^{33}P]$ATP (10 μL). After incubating for 30 minutes, the reaction is quenched by simple removal of the reaction buffer and each well is washed twice with 300 μl of Tris/HCl buffer. The radioactivity is then measured in each well using a Packard, Top-Count model scintillation machine.

The control enzymatic activity of Aurora is expressed by the number of counts per minute obtained over 30 minutes after subtracting the background noise (reaction mixture containing no enzyme). The evaluation of the various test products is expressed as a percentage of inhibition of the Aurora activity relative to the control. In this test, the compounds inhibit the kinases Aurora1 and Aurora2 at concentrations generally of between 1 nM and 10 μM, and preferably less than 2 μM.

Determination of the Inhibition of the Kinase Tie2:

The coding sequence of human Tie2 corresponding to the amino acids of the intracellular domain 776-1124 was generated by PCR using the cDNA isolated from a human placenta as a model. This sequence was introduced into a pFastBacGT baculovirus expression vector in the form of a GST fusion protein.

The inhibitory effect of the molecules is determined in a test of phosphorylation of PLC with Tie2 in the presence of GST-Tie2 purified to about 80% homogeneity. The substrate is composed of the SH2-SH3 fragments of PLC expressed in the form of a GST fusion protein.

The kinase activity of Tie2 is measured in a MOPS 20 mM pH 7.2 buffer, containing 10 mM $MgCl_2$, 10 mM $MnCl_2$, 1 mM DTT, 10 mM of glycerophosphate. In a 96-well Flash-Plate plate maintained on ice, a reaction mixture is deposited, composed of 70 μL of kinase buffer containing 100 ng of enzyme GST-Tie2 per well. Next, 10 μL of the test molecule diluted in DMSO to a maximum concentration of 10% are added. For a given concentration, each measurement is performed four times. The reaction is initiated by adding 20 μL of solution containing 2 μg of GST-PLC, 2 μm of cold ATP and 1 μCi of $^{33}P[ATP]$. After incubation for one hour at 37° C., the reaction is stopped by adding 1 volume (100 μl) of 200 mM EDTA. After removal of the incubation buffer, the wells are washed three times with 300 μL of PBS. The radioactivity is measured on a MicroBeta1450 Wallac.

The inhibition of the Tie2 activity is calculated and expressed as a percentage of inhibition relative to the control activity determined in the absence of compound. The compounds inhibit the kinase Tie2 at concentrations generally of between 1 nM and 10 μM.

The compounds of the invention are thus inhibitors of the kinases Aurora1, Aurora2 and Tie2. Consequently, they may be used for the preparation of medicaments, in particular of medicaments for inhibiting the kinases Aurora1, Aurora2 and Tie2.

The invention claimed is:

1. A compound of formula (I):

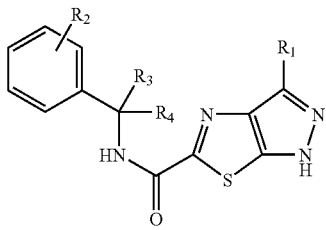

in which:

R$_1$ represents a group —NHR$_5$, in which R$_5$ is selected from a hydrogen atom and a group —COR$_6$, in which R$_6$ is selected from a hydrogen atom and an alkyl, alkenyl, alkynyl, cycloalkyl, cycloalkenyl, heterocycloalkyl, heterocycloalkenyl, aryl, heteroaryl, alkylaryl, alkylheteroaryl, -aryl-alkyl, -aryl-cycloalkyl, -aryl-alkyl-cycloalkyl, -aryl-heterocycloalkyl, -aryl-alkyl-heterocycloalkyl, -heteroaryl-alkyl, -heteroaryl-heterocycloalkyl and -heteroaryl-alkyl-heterocycloalkyl group, in which the R$_6$ substituents are optionally substituted with one or more group(s), which may be identical to or different from each other, selected from halogen atoms and alkoxy, oxo, —OH, —CH$_2$OH, —NO$_2$, —CN, —COOH, —COO-alkyl, haloalkyl, haloalkoxy, CONR$_7$R$_8$, NR$_7$R$_8$ and a S(O)$_x$Me group, in which R$_7$ and R$_8$ represent, independently of each other, a hydrogen atom or an alkyl, cycloalkyl or haloalkyl group and in which x is a value from 0 to 2;

R$_2$ represents a hydrogen atom or one or more substituent(s) of the phenyl ring independently selected from a halogen atom, an alkyl, alkoxy, —OH, -haloalkyl, —NO$_2$, —CN, —COOH, —COO-alkyl, haloalkoxy, -heteroaryl, -heterocycloalkyl, CONR$_7$R$_8$, NR$_7$R$_8$ and a S(O)$_x$Me group, in which the alkyl and alkoxy groups are optionally substituted with one or more groups, which may be identical to or different from each other, chosen from halogen atoms and alkoxy, —OH, haloalkyl, —NO$_2$, —CN, —COOH, —COO-alkyl, haloalkoxy, CONR$_7$R$_8$, NR$_7$R$_8$ and S(O)$_x$Me groups, in which R$_7$, R$_8$ and x are as defined above; and R$_3$ and R$_4$ represent an alkyl group optionally substituted with one or more groups, which may be identical to or different from each other, chosen from halogen atoms and alkoxy, —OH, haloalkyl, —NO$_2$, —CN, —COOH, —COOalkyl, haloalkoxy, CONR$_7$R$_8$, NR$_7$R$_8$ and a S(O)$_x$Me group, in which R$_3$ and R$_4$ form, together with the carbon to which they are attached, a 3- to 6-membered cycloalkyl group, optionally substituted with one or more groups, which may be identical to or different from each other, chosen from halogen atoms and -alkyl, -alkoxy, —OH, haloalkyl, haloalkoxy, —NO$_2$, —CN, —COOH, —COO-alkyl, CONR$_7$R$_8$, NR$_7$R$_8$ and S(O)$_x$Me groups, in which R$_7$, R$_8$ and x are as defined above;

or a salt thereof.

2. The compound according to claim 1, wherein

R$_1$ represents a group —NHR$_5$, in which R$_5$ is selected from a hydrogen atom and a group —COR$_6$, in which R$_6$ is selected from a hydrogen atom and a group —(C$_1$-C$_6$)alkyl, —(C$_1$-C$_6$)alkenyl, —(C$_1$-C$_6$)alkynyl, —(C$_3$-C$_7$)cycloalkyl, —(C$_3$-C$_7$)cycloalkenyl, —(C$_3$-C$_7$)heterocycloalkyl, —(C$_3$-C$_7$)heterocycloalkenyl, —(C$_6$-C$_{14}$)aryl, —(C$_4$-C$_{14}$)heteroaryl, —(C$_1$-C$_6$)alkyl-aryl, —(C$_1$-C$_6$)alkyl-heteroaryl, -aryl-(C$_1$-C$_6$)alkyl, -aryl-(C$_0$-C$_3$)alkyl-cycloalkyl, -aryl-(C$_0$-C$_3$)alkyl-heterocycloalkyl, -heteroaryl-(C$_1$-C$_6$)alkyl and -heteroaryl -(C$_0$-C$_3$)alkyl-heterocycloalkyl, in which the R$_6$ substituents are optionally substituted with one or more group(s), which may be identical to or different from each other, selected from halogen atoms and —(C$_1$-C$_6$)alkoxy, oxo, —OH, —CH$_2$OH, —NO$_2$, —CN, —COOH, —COO—(C$_1$-C$_4$)alkyl, haloalkyl, haloalkoxy, CONR$_7$R$_8$, NR$_7$R$_8$ and a S(O)$_x$Me group, in which R$_7$ and R$_8$ represent, independently, of each other, a hydrogen atom or a —(C$_1$-C$_4$)alkyl, cycloalkyl or haloalkyl group and in which x is a value from 0 to 2;

R$_2$ represents a hydrogen atom or one or more substituents(s) of the phenyl ring independently selected from a halogen atom, a —(C$_1$-C$_4$)alkyl, —(C$_1$-C$_6$)alkoxy, —OH, haloalkyl, —NO$_2$, —CN or —COOH group and a —COO—(C$_1$-C$_4$)alkyl, haloalkoxy, —(C$_4$-C$_{14}$)heteroaryl, —(C$_3$-C$_7$)heterocycloalkyl, —CONR$_7$R$_8$, —NR$_7$R$_8$ and a —S(O)$_x$Me group, in which the alkyl and alkoxy groups are optionally substituted with one or more group(s), which may be identical to or different from each other, chosen from halogen atoms and —(C$_1$-C$_4$)alkoxy, —OH, haloalkyl, —NO$_2$, —CN, —COOH, —COO—(C$_1$-C$_4$)alkyl, haloalkoxy, —CONR$_7$R$_8$, —NR$_7$R$_8$ and —S(O)$_x$Me groups, in which R$_7$, R$_8$ and x are as defined above; and R$_3$ and R$_4$ represent a —(C$_1$-C$_4$)alkyl group optionally substituted with one or more group(s), which may be identical to or different from each other, chosen from halogen atoms and —(C$_1$-C$_4$)alkoxy, —OH, haloalkyl, —NO$_2$, —CN, —COOH, —COOalkyl, haloalkoxy, —CONR$_7$R$_8$, —NR$_7$R$_8$ and —S(O)$_x$Me groups, or R$_3$ and R$_4$ form, together with the carbon atom to which they are attached, a 3- to 6-membered cycloalkyl group, optionally substituted with one or more group(s), which may be identical to or different from each other, chosen from halogen atoms and —(C$_1$-C$_4$)alkyl, —(C$_1$-C$_4$)alkoxy, —OH, haloalkyl, haloalkoxy, —NO$_2$, —CN, —COOH, —COO—(C$_1$-C$_4$)alkyl, —CONR$_7$R$_8$, —NR$_7$R$_8$ and —S(O)$_x$Me groups, in which R$_7$, R$_8$ and x are as defined above;

or a salt thereof.

3. The compound according to claim 1, wherein R$_7$ and R$_8$ represent, independently of each other, a hydrogen atom or a —(C$_1$-C$_4$)alkyl group; or a salt thereof.

4. The compound according to claim 1, wherein R$_3$ and R$_4$ each represent a methyl group; or a salt thereof.

5. The compound according to claim 1, wherein R$_2$ represents a hydrogen atom; or a salt thereof.

6. The compound according to claim 1, wherein R$_6$ is chosen from an aryl or heteroaryl group, optionally substituted with a halogen atom, —(C$_1$-C$_3$)alkoxy or —(C$_0$-C$_3$)alkyl-heterocycloalkyl; or a salt thereof.

7. The compound according to claim 6, wherein the aryl group is a phenyl and the heteroaryl group is a thienyl or a pyridine; or a salt thereof.

8. The compound according to claim 6, wherein the heterocycloalkyl is of the form:

or a salt thereof.

9. The compound according to claim 6, wherein the heterocycloalkyl is chosen from morpholinyl, piperazinyl, pyrrolidinyl and piperidyl; or a salt solvate.

10. A compound of formula (I):

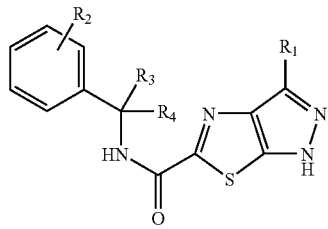

in which:
- $R_1$ represents a group —$NHR_5$, in which $R_5$ is a group —$COR_6$, wherein $R_6$ represents a phenyl substituted with a —$(C_1-C_3)$alkyl-$NR_9R_{10}$ group, in which $R_9$ and $R_{10}$ are independently selected from the group consisting of H, —$(C_1-C_6)$alkyl, aryl, heteroaryl, —$(C_1-C_6)$alkyl-aryl and —$(C_1-C_6)$alkyl-heteroaryl, which are optionally substituted;
- $R_2$ represents a hydrogen atom or one or more substituent(s) of the phenyl ring independently selected from a halogen atom, an alkyl, alkoxy, —OH, -haloalkyl, —$NO_2$, —CN, —COOH, —COO-alkyl, haloalkoxy, -heteroaryl, -heterocycloalkyl, $CONR_7R_8$, $NR_7R_8$ and a $S(O)_x$Me group, in which the alkyl and alkoxy groups are optionally substituted with one or more groups, which may be identical to or different from each other, chosen from halogen atoms and alkoxy, —OH, haloalkyl, —$NO_2$, —CN, —COOH, —COO-alkyl, haloalkoxy, $CONR_7R_8$, $NR_7R_8$ and $S(O)_x$Me groups, in which $R_7$ and $R_8$ represent, independently of each other, a hydrogen atom or an alkyl, cycloalkyl or haloalkyl group and in which x is a value from 0 to 2; and
- $R_3$ and $R_4$ represent an alkyl group optionally substituted with one or more groups, which may be identical to or different from each other, chosen from halogen atoms and alkoxy, —OH, haloalkyl, —$NO_2$, —CN, —COOH, —COOalkyl, haloalkoxy, $CONR_7R_8$, $NR_7R_8$ and a $S(O)_x$Me group, in which $R_3$ and $R_4$ form, together with the carbon to which they are attached, a 3- to 6-membered cycloalkyl group, optionally substituted with one or more groups, which may be identical to or different from each other, chosen from halogen atoms and -alkyl, -alkoxy, —OH, haloalkyl, haloalkoxy, —$NO_2$, —CN, —COOH, —COO-alkyl, $CONR_7R_8$, $NR_7R_8$ and $S(O)_x$Me groups, in which $R_7$, $R_8$ and x are as defined above; or a salt thereof.

11. A compound selected from the group consisting of:
N-(1-methyl-1-phenylethyl)(3-amino-1H-pyrazolo[4,3-d]thiazole)-5-carboxamide;
N-(1-methyl-1-phenylethyl)-3-[4-(4-methylpiperazin-1-yl)benzoylamino]-1H-pyrazolo[4,3-d]thiazole-5-carboxamide;
N-(1-methyl-1-phenylethyl)-3-(4-morpholin-4-ylbenzoylamino)-1H-pyrazolo[4,3-d]thiazole-5-carboxamide;
N-(1-methyl-1-phenylethyl)-3-(4-methoxybenzoylamino)-1-H-pyrazolo[4,3-d]thiazole-5-carboxamide;
N-(1-methyl-1-phenylethyl)-3-[(thiophene-3-carbonyl)amino]-1H-pyrazolo[4,3-d]thiazole-5-carboxamide;
N-(1-methyl-1-phenylethyl)-3-(4-morpholin-4-ylmethyl-benzoylamino)-1H-pyrazolo[4,3-d]thiazole-5-carboxamide;
N-(1-methyl-1-phenylethyl)-3-[4-(4-methylpiperazin-1-ylmethyl)benzoylamino]-1H-pyrazolo[4,3-d]thiazole-5-carboxamide;
N-(1-methyl-1-phenylethyl)-3-(4-piperidin-1-ylmethyl-benzoylamino)-1H-pyrazolo[4,3-d]thiazole-5-carboxamide;
N-(1-methyl-1-phenylethyl)-3-(4-pyrrolidin-1-ylmethyl-benzoylamino)-1H-pyrazolo[4,3-d]thiazole-5-carboxamide;
N-(1-methyl-1-phenylethyl)-3-{[4-(4-methyl-piperazin-1-yl)thiophene-2-carbonyl]amino}-1H-pyrazolo[4,3-d]thiazole-5-carboxamide;
N-(1-methyl-1-phenylethyl)-3-{[5-(4-methylpiperazin-1-yl)thiophene-2-carbonyl]amino}-1H-pyrazolo[4,3-d]thiazole-5-carboxamide;
N-(1-methyl-1-phenylethyl)-3-[(pyridine-2-carbonyl)amino]-1H-pyrazolo[4,3-d]thiazole-5-carboxamide;
N-(1-methyl-1-phenylethyl)-3-[(pyridine-3-carbonyl)amino]-1H-pyrazolo[4,3-d]thiazole-5-carboxamide;
N-(1-methyl-1-phenylethyl)-3-[(pyridine-4-carbonyl)amino]-1H-pyrazolo[4,3-d]thiazole-5-carboxamide;
N-(1-methyl-1-phenylethyl)-3-{[2-(4-methylpiperazin-1-yl)pyridine-4-carbonyl]amino}-1H-pyrazolo[4,3-d]thiazole-5-carboxamide;
N-(1-methyl-1-phenylethyl)-3-{[6-(4-methylpiperazin-1-yl)pyridine-2-carbonyl]amino}-1H-pyrazolo[4,3-d]thiazole-5-carboxamide; and
N-(1-methyl-1-phenylethyl)-3-{[6-(4-methylpiperazin-1-yl)pyridine-3-carbonyl]amino}-1H-pyrazolo[4,3-d]thiazole-5-carboxamide;

or a salt thereof.

12. A pharmaceutical composition comprising a compound according to claim 1, or a pharmaceutically acceptable salt thereof, in combination with at least one pharmaceutically acceptable excipient.

13. A pharmaceutical composition comprising a compound according to claim 2, or a pharmaceutically acceptable salt thereof, in combination with at least one pharmaceutically acceptable excipient.

14. A pharmaceutical composition comprising a compound according to claim 10 or a pharmaceutically acceptable salt thereof, in combination with at least one pharmaceutically acceptable excipient.

15. A pharmaceutical composition comprising a compound according to claim 11, or a pharmaceutically acceptable salt thereof, in combination with at least one pharmaceutically acceptable excipient.

16. A method for inhibiting a kinase selected from the group consisting of Aurora1, Aurora2 and Tie2, which comprises administering to a patient in need of said inhibition an effective amount of a compound of formula (I) or a pharmaceutically acceptable salt thereof, according to claim 1.

17. A process for preparing a compound of formula (Ib):

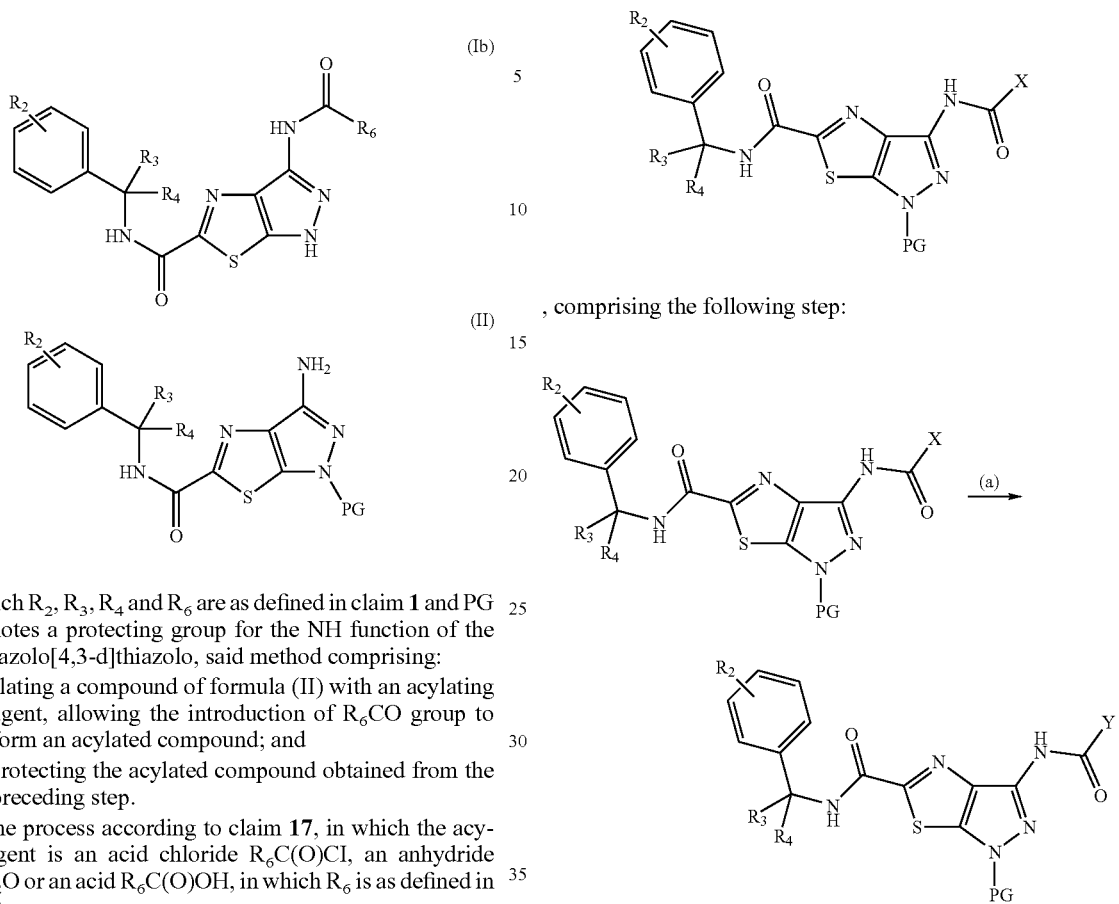

in which $R_2$, $R_3$, $R_4$ and $R_6$ are as defined in claim 1 and PG denotes a protecting group for the NH function of the pyrazolo[4,3-d]thiazolo, said method comprising:
  acylating a compound of formula (II) with an acylating agent, allowing the introduction of $R_6CO$ group to form an acylated compound; and
  deprotecting the acylated compound obtained from the preceding step.

18. The process according to claim 17, in which the acylating agent is an acid chloride $R_6C(O)Cl$, an anhydride $(R_6CO)_2O$ or an acid $R_6C(O)OH$, in which $R_6$ is as defined in claim 19.

19. The process according to claim 17, in which the acelating step is preceded by a step of protecting the NH function of the compound of formula (Ia) with the protecting group PG:

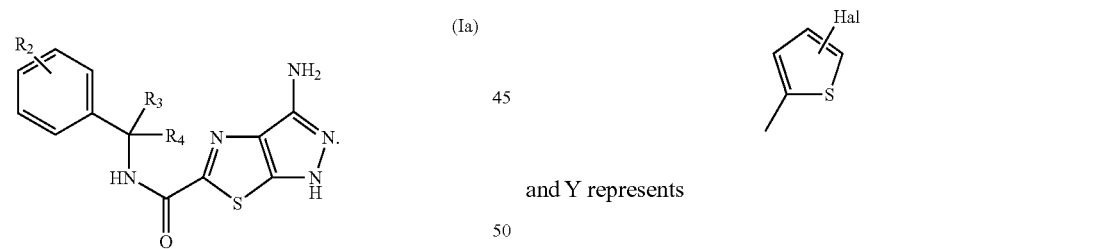

20. A process for preparing a compound of formula

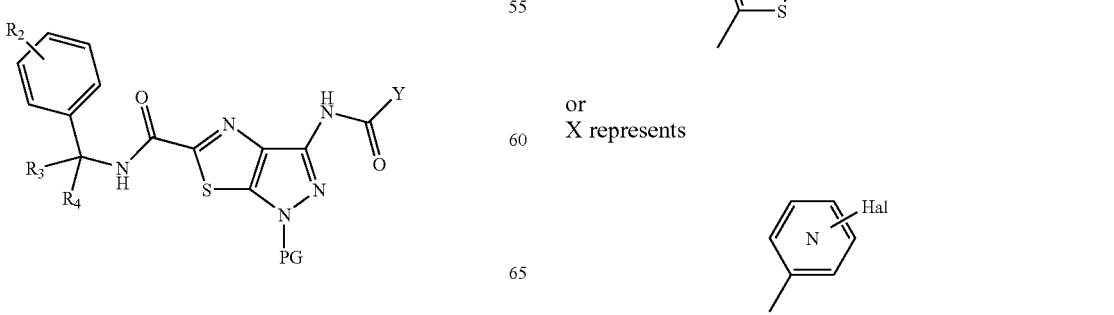

from a compound of formula

, comprising the following step:

in which:
X represent and Y represents or
X represents and Y represents
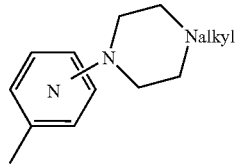
or alternatively
X represents
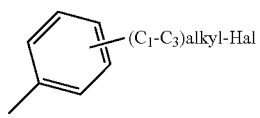
and Y represents
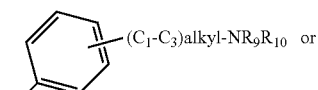
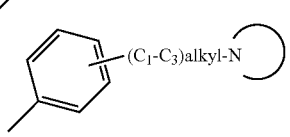
or
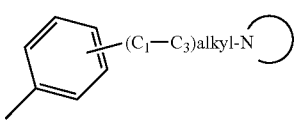
and in which $R_2$, $R_3$, $R_9$, $R_{10}$ and PG are as defined in claim 1.
21. A compound selected from the group consisting of:
(3)
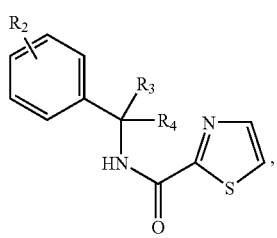
(4)
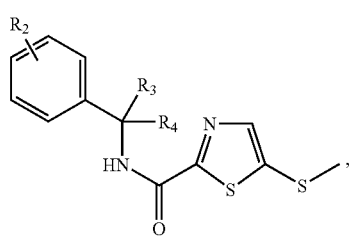
(5)
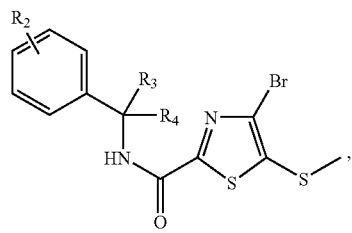
(6)
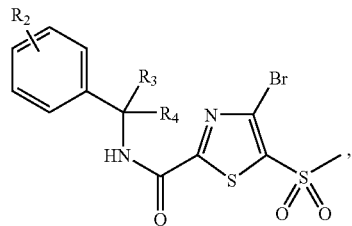
(7)
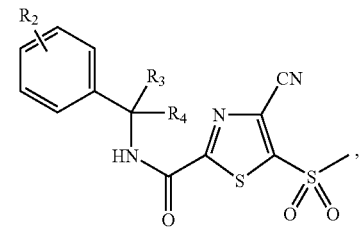
(8)
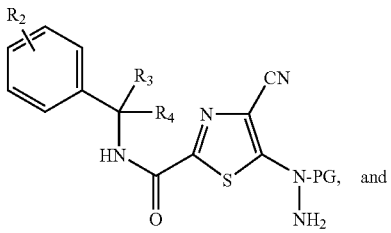
(II)
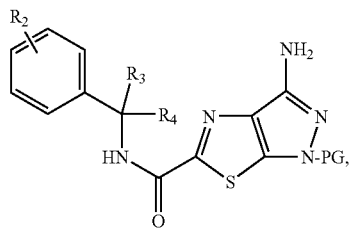
in which $R_2$, $R_3$, $R_4$ and PG are as defined in claim 1.
22. A compound selected from the group consisting of:
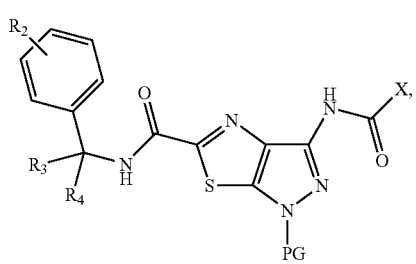

-continued
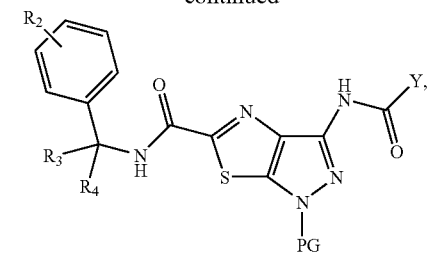
and in which $R_2$, $R_3$, $R_4$ and PG are as defined in claim 1; and
X represents
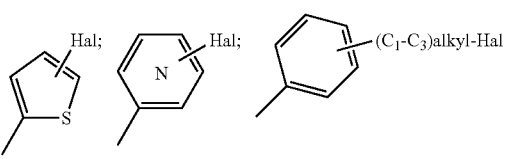
Y represents
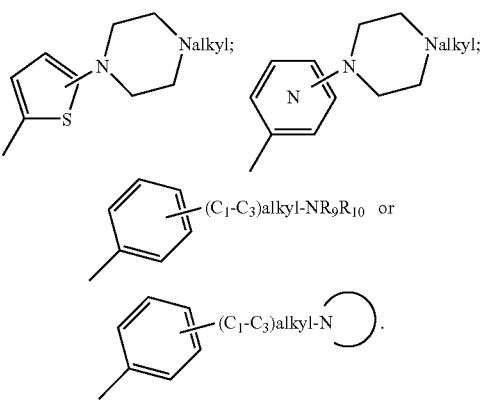
* * * * *

UNITED STATES PATENT AND TRADEMARK OFFICE
CERTIFICATE OF CORRECTION

PATENT NO.        : 7,772,261 B2
APPLICATION NO.   : 12/356740
DATED             : August 10, 2010
INVENTOR(S)       : Gilles Doerflinger et al.

It is certified that error appears in the above-identified patent and that said Letters Patent is hereby corrected as shown below:

On the Title page Item (56), under "Other Publications", line 29, delete "Anglogenesis" and insert -- Angiogenesis --, therefor.

In column 1, line 47, delete "3-d" and insert -- 3-c --, therefor.

In column 1, line 48, delete "X=S" and insert -- X=S --, therefor.

In column 1, line 45-46, delete "suberates" and insert -- suberites --, therefor.

In column 12, line 16, delete "suramine" and insert -- suramin --, therefor.

In column 13, line 54, delete "Verleg" and insert -- Verlag --, therefor.

In column 20, in Structure 3, line 40-59, delete " 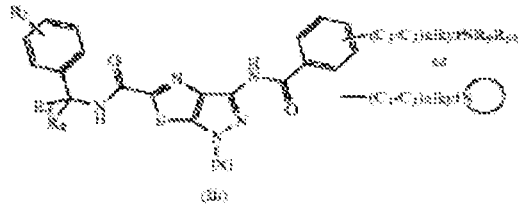 " and insert -- 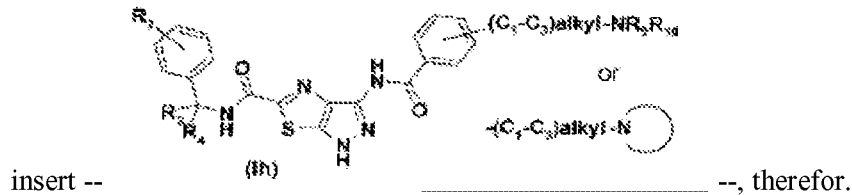 --, therefor.

Signed and Sealed this
Seventeenth Day of May, 2011

David J. Kappos
*Director of the United States Patent and Trademark Office*

CERTIFICATE OF CORRECTION (continued)

In column 24, line 6-11, delete "The product abundance was measured using a diode array detector over a wavelength range from 210 to 400 nm. The mass spectra were acquired over a range from 100 to 1200 atomic mass units. The data were analysed using the Micromass MassLynx software. The main ions observed are described." and insert the same on Col. 24, line 5, as a continuation of the paragraph.

In column 24, line 21-22, delete "$R_1$=$NH_2$, $R_5$=H, $R_3$=$R_4$=Me, $R_2$=H)" and insert -- $R_1$=$NH_2$, $R_5$=H, $R_3$=$R_4$=Me, $R_2$=H) --, therefor.

In column 33, line 39, delete "haemoangioma" and insert -- haemangioma --, therefor.

In column 34, line 30, delete "pFastBacGT" and insert -- pFastBacHT --, therefor.

In column 37, line 11, in claim 9, delete "solvate." and insert -- thereof. --, therefor.

In column 39, line 34, in claim 18, delete "$R_6C(O)Cl$" and insert -- $R_6C(O)Cl$ --, therefor.

In column 40, line 39, in claim 20, delete "represent" and insert -- represents --, therefor.

In column 41, in structure 5, line 34-41, in claim 20, before "and" delete "  ".